US008927485B2

(12) United States Patent
Krantz et al.

(10) Patent No.: US 8,927,485 B2
(45) Date of Patent: Jan. 6, 2015

(54) SITE-SPECIFIC MODIFICATION OF PROTEINS THROUGH CHEMICAL MODIFICATION ENABLING PROTEIN CONJUGATES, PROTEIN DIMER FORMATION, AND STAPLED PEPTIDES

(75) Inventors: Alexander Krantz, Boston, MA (US); Peng Yu, Malden, MA (US)

(73) Assignee: Advanced Proteome Therapeutics Inc., Boston, MA (US)

( * ) Notice: Subject to any disclaimer, the term of this patent is extended or adjusted under 35 U.S.C. 154(b) by 139 days.

(21) Appl. No.: 13/030,772

(22) Filed: Feb. 18, 2011

(65) Prior Publication Data

US 2011/0263832 A1 Oct. 27, 2011

Related U.S. Application Data

(60) Provisional application No. 61/338,382, filed on Feb. 18, 2010, provisional application No. 61/340,298, filed on Mar. 15, 2010.

(51) Int. Cl.
| A61K 38/00 | (2006.01) |
| C07K 16/00 | (2006.01) |
| C07K 17/00 | (2006.01) |
| C07K 17/14 | (2006.01) |
| C12P 21/08 | (2006.01) |
| A61K 38/24 | (2006.01) |
| A61K 38/27 | (2006.01) |
| C07K 1/00 | (2006.01) |
| C07K 14/00 | (2006.01) |
| A61K 47/48 | (2006.01) |

(52) U.S. Cl.
CPC .................................. *A61K 47/481* (2013.01)
USPC ........................ 514/1.1; 530/391.1; 530/399

(58) Field of Classification Search
CPC .................................................. A61K 47/481
See application file for complete search history.

(56) References Cited

U.S. PATENT DOCUMENTS

| 5,900,404 | A | 5/1999 | Gegg et al. |
| 6,017,876 | A | 1/2000 | Gegg et al. |
| 6,204,247 | B1 | 3/2001 | Gegg et al. |
| 6,326,468 | B1 * | 12/2001 | Canne et al. .................. 506/30 |
| 6,420,340 | B2 | 7/2002 | Gegg et al. |
| 2003/0215877 | A1 | 11/2003 | Love et al. |
| 2005/0079208 | A1 * | 4/2005 | Albani .......................... 424/450 |
| 2007/0123465 | A1 * | 5/2007 | Adermann et al. ............ 514/12 |

FOREIGN PATENT DOCUMENTS

| WO | WO 2005/074650 | * | 8/2005 |
| WO | WO 2007/112362 | * | 10/2007 |

OTHER PUBLICATIONS

Gilmore et al, N-Terminal Protein Modification through a Biomimetic Transamination Reaction, Angew. Chem. Int. Ed, 2006, 45, 5307-5311.*

Deady et al, Synthesis and Antitumor Activity of Some Indeno[1,2-b]quinoline-based bis Carboxamides, Bioorganic & Medicinal Chemistry 8 (2000) 977-984.*
Wen et al, Erythropoietin Structure-Function Relationships: High Degree of Sequence Homology Among Mammals, Blood, vol. 82, No. 5 (Sep. 1, 1993): pp. 1507-1516.*
Deady et al, Synthesis and Antitumor Activity of Some Indeno[1,2-b]quinoline-based bis Carboxamides, Bioorganic & Medicinal Chemistry 8 (2000) 977-98.*
Niemeyer et al., "Oligonucleotide-Directed Self Assembly of Proteins: Semisynthetic DNA—Streptavidin Hybrid Molecules as Connectors for the Generation of Macroscopic Arrays and the Construction of Supramolecular Bioconjugates," *Nucleic Acids Research* 22:5530-5539 (1994).
Wang et al., "Interaction of a Self-Assembling Peptide with Oligonucleotides: Complexation and Aggregation," *Biophysical Journal* 93:2477-2490 (2007).
International Search Report (PCT/US1125413), completed Jun. 28, 2011, mailed Jul. 15, 2011.
Blanco-Canosa et al., "An efficient Fmoc-SPPS approach for the generation of thioester peptide precursors for use in native chemical litigation," Angew Chem Int Ed Engl. 47(36):6851-6855 (2008).
Dixon, "N-terminal modification of proteins—A review," J Protein Chem. 3(1):99-108, 1984.
Gentle et al., "Direct production of proteins with N-terminal cysteine for site-specific conjugation," Bioconjug Chem. 15(3):658-663 (2004).
Hauser et al., "Expressed protein ligation using an N-terminal cysteine containing fragment generated in vivo from a pelB fusion protein," Protein Expr Purif. 54(2):227-233 (2007).
Johnson et al., "Insights into the mechanism and catalysis of the native chemical ligation reaction," J Am Chem Soc. 128(20):6640-6646 (2006).
Kalia et al., "Hydrolytic stability of hydrazones and oximes,"Angew Chem Int Ed Engl. 47(39):7523-7526 (2008).
Kent, "Total chemical synthesis of proteins," Chem Soc Rev. 38(2):338-351 (2009).
Kolb et al., "Click chemistry: diverse chemical function from a few good reactions," Angew Chem Int Ed. 40(11):2004-2021 (2001).
Nishimura et al., "An efficient chemical method for removing N-terminal extra methionine from recombinant methionylated human growth hormone," Chem Commun. 1135-1136 (1998).

(Continued)

*Primary Examiner* — Marcela M Cordero Garcia
*Assistant Examiner* — Sergio Coffa
(74) *Attorney, Agent, or Firm* — Clark & Elbing LLP

(57) ABSTRACT

The present invention generally provides methods for the site-specific modification of peptides, polypeptides, and proteins, e.g., granulocyte macrophage colony-stimulating factor, human superoxide dismutase, annexin, leptin, antibodies and the like, cytokines and chemokines, at their N-termini and at sites at which unnatural aminoacids have been introduced along the protein framework. The modifications described herein can be used for the synthesis and application of the adducts in radio-labeling, molecular imaging and protein therapeutic applications, and the treatment of disorders such as rheumatoid arthritis, lupus erythematosus, psoriasis, multiple sclerosis, type-1 diabetes, Crohn's disease, and systemic sclerosis, Alzheimer disease, cancer, liver disease (e.g., alcoholic liver disease), and cachexia.

9 Claims, No Drawings

(56) References Cited

OTHER PUBLICATIONS

Radić et al., "Probing gorge dimensions of cholinesterases by freeze-frame click chemistry," Chem Biol Interact. 175(1-3):161-165 (2008).
Selden et al., "Cross-linked dimers with nucleating activity in actin prepared from muscle acetone powder," Biochemistry. 39:64-74 (2000).
Sunde et al., "Improved conditions for the removal of 2-oxoacyl groups from the N-terminus of proteins," Biochim Biophys Acta. 1388(1):45-52 (1998).
Tam et al., "Orthogonal ligation strategies for peptide and protein," Biopolymers. 51(5):311-332 (1999).
Witus et al., "Identification of highly reactive sequences for PLP-mediated bioconjugation using a combinatorial peptide library," J Am Chem Soc. 132(47):16812-16817 (2010).
International Preliminary Report on Patentability for International Application No. PCT/US2011/025413, dated on Aug. 21, 2012 (1 page).
Written Opinion of the International Search Authority for International Application No. PCT/US11/25413, dated Jul. 15, 2011(5 pages).

* cited by examiner

US 8,927,485 B2

SITE-SPECIFIC MODIFICATION OF PROTEINS THROUGH CHEMICAL MODIFICATION ENABLING PROTEIN CONJUGATES, PROTEIN DIMER FORMATION, AND STAPLED PEPTIDES

CROSS-REFERENCE TO RELATED APPLICATIONS

This application claims benefit of U.S. Provisional Application Nos. 61/338,382, filed Feb. 18, 2010, and 61/340,298, filed Mar. 15, 2010, which are hereby incorporated by reference in their entirety.

FIELD OF THE INVENTION

The present invention generally provides methods for the site-specific modification of peptides, polypeptides, and proteins, e.g., granulocyte macrophage colony-stimulating factor, human superoxide dismutase, annexins, leptin, antibodies and the like, cytokines and chemokines, at their N-termini or at unnatural amino acids introduced along the peptide framework. The modifications described herein can be used for the synthesis and application of the adducts in radio-labeling, molecular imaging and protein therapeutic applications, and the treatment of disorders such as rheumatoid arthritis, lupus erythematosus, psoriasis, multiple sclerosis, type-1 diabetes, Crohn's disease, and systemic sclerosis, Alzheimer disease, cancer, liver disease (e.g., alcoholic liver disease), and cachexia.

BACKGROUND OF THE INVENTION

Protein conjugation lies at the heart of the discovery and development of protein therapeutics. Chemical modification strategies typically employ a two step process where the first step involves site-specific modification of the protein and the second step is the installation of an entity of interest. The selectivity of the second step is often a consequence of the chemospecific reactivity of a donor-acceptor pair, e.g., aminooxy donor-carbonyl acceptor, whose reactivity is orthogonal to that of peptide side-chains. (Tam et al., *Biopolymers*. 51:311-32, 1999)

The first step involving modification of the protein can be difficult to effect site-specifically by chemical methods in view of the presence of many peptide residues of the same type. Accordingly, limited success has been achieved in such site-specific modifications, although enzymes have been used to effect these transformations. For example, it has been demonstrated that group modification agents with minimal binding determinants can sometimes react site-specifically due to enzyme active sites, e.g., active site serines of proteinases (Means et al., *Chemical Modification of Proteins*, Holden-Day, Inc., San Francisco, 1971.)

For proteins that have not evolved to do such chemistry, the challenges for site-specific labeling are far greater than for the construction of active-site directed reagents. For such proteins the challenges can be likened to the development of site-specific modifications of non-active site residues of enzymes. Thus, other than for active-sites, and allosteric sites that have evolved to bind enzyme modulators, site-specific labeling reagents (affinity labels) are lacking and novel approaches are required to fill that void. Amino acid residues usually have little to distinguish their reactivity from others in the same class, with the exception of cysteine thiols whose chemistry is quite distinct from other peptidic side chain functionality. Alternatively, strategies for the installation of functional groups that can engage in orthogonal conjugative reactions can be useful for the selective modification of proteins.

For these reasons, methods for the site-specific modification and ligation of proteins would be useful for the synthesis of modified peptide, polypeptide, and protein adducts and use of the adducts in radio-labeling, molecular imaging and protein therapeutic applications, and in methods of medical treatment.

SUMMARY OF THE INVENTION

The present invention generally provides site-specific modifications of peptides, polypeptides, and proteins at their N-termini. The present invention further provides methods of making and using the adducts as intermediates in the preparation of radio-labelling and molecular imaging agents, and protein therapeutics in the treatment of disorders such as rheumatoid arthritis, lupus erythematosus, psoriasis, multiple sclerosis, type-1 diabetes, Crohn's disease, and systemic sclerosis, Alzheimer disease, cancer, liver disease (e.g., alcoholic liver disease), and cachexia.

In one aspect, the invention features a method of synthesizing a compound having a structure according to Formula (V),

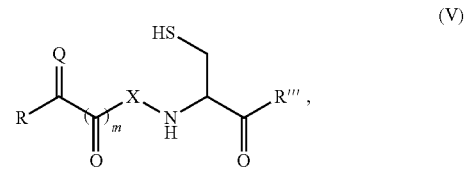

or a salt or solvate thereof, where the method includes
(a) a compound having a structure according to Formula (II),

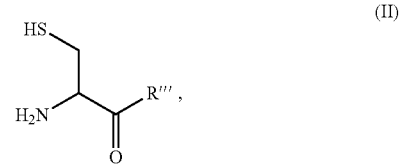

where R''' is a protein; and
(b) a compound having a structure according to Formula (IV),

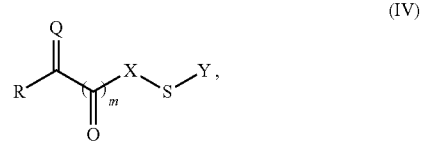

where
R is H, optionally substituted $C_{1-20}$ alkyl, optionally substituted $C_{2-20}$ alkynyl, optionally substituted $C_{6-14}$ aryl, or optionally substituted 5-14 membered heteroaryl;
Q is O or $W(O)_{p1}(CH_2)_q(O)_{p2}$-L;
W is N, NNH, or NNHCO;
each of p1 and p2 is, independently, 0 or 1;

q is an integer between 1-20;

L is —N=(Bio), —NHN=(Bio), CONHN=(Bio), NH-(Bio), NHNH-(Bio), where Bio is a biologically active agent covalently attached to nitrogen via a single or double bond as shown;

Y is optionally substituted $C_{1-20}$ alkyl or optionally substituted $C_{6-14}$ aryl; and where m and X are defined as follows,
  (i) m is 1 when X is —[NHCH(R')C(=O)]$_n$, wherein n is an integer between 0-20 and R' is the side chain of any natural or unnatural α-amino acid;
  (ii) m is 1 when X is [NH(CH$_2$)$_n$C(=O)], wherein n is an integer between 0 and 20;
  (iii) m is 1 when X is [NZ(CH$_2$CH$_2$O)$_{n'}$(CH$_2$)$_{q'}$C(=O)], wherein Z is H or optionally substituted $C_{1-20}$ alkyl, n' is an integer between 0-10,000, and q' is an integer between 2-4;
  (iv) m is 0 when X is [(CH$_2$)$_q$\{NCH(R')C(=O)\}$_n$], wherein q is an integer between 1-20, n is an integer between 0-20, and R' is the side chain of any natural or unnatural α-amino acid;
  (v) m is 0 when X is [(CH$_2$)$_n$C(=O)], wherein n is an integer between 0-20; and
  (vi) m is 0 when X is [(CH$_2$CH$_2$O)$_{n'}$(CH$_2$)$_{q'}$C(=O)], wherein n' is an integer between 0-10,000 and q' is an integer between 2-4.

In some embodiments, Q is O. In other embodiments, Q is W(O)$_{p1}$(CH$_2$)$_q$(O)$_{p2}$-L.

In certain embodiments, Bio is selected from a pharmaceutical, an imaging moiety, or an antibody.

In other embodiments, R''' is a four helix bundle protein.

In another aspect, the invention relates to a compound having a structure having a structure according to the following formula,

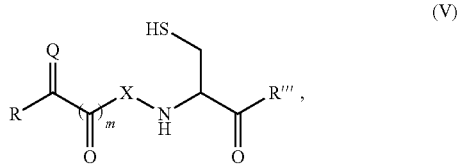

(V)

or a salt or solvate thereof, where

R is H, optionally substituted $C_{1-20}$ alkyl, optionally substituted $C_{2-20}$ alkynyl, optionally substituted $C_{6-14}$ aryl, or optionally substituted 5-14 membered heteroaryl;

Q is O or W(O)$_{p1}$(CH$_2$)$_q$(O)$_{p2}$-L;

W is N, NNH, or NNHCO;

each of p1 and p2 is, independently, 0 or 1;

q is an integer between 1-20;

L is —N=(Bio), —NHN=(Bio), CONHN=(Bio), NH-(Bio), NHNH-(Bio), wherein Bio is a biologically active agent covalently attached to nitrogen via a single or double bond as shown;

R''' is a protein; and wherein m and X are defined as follows,
  (i) m is 1 when X is —[NHCH(R')C(=O)]$_n$, wherein n is an integer between 0-20 and R' is the side chain of any natural or unnatural α-amino acid;
  (ii) m is 1 when X is [NH(CH$_2$)$_n$C(=O)], wherein n is an integer between 0 and 20;
  (iii) m is 1 when X is [NZ(CH$_2$CH$_2$O)$_{n'}$(CH$_2$)$_{q'}$(=O)], wherein Z is H or optionally substituted $C_{1-20}$ alkyl, n' is an integer between 0-10,000, and q' is an integer between 2-4;
  (iv) m is 0 when X is [(CH$_2$)$_q$\{NCH(R')C(=O)\}$_n$], wherein q is an integer between 1-20, n is an integer between 0-20, and R' is the side chain of any natural or unnatural α-amino acid;
  (v) m is 0 when X is [(CH$_2$)$_n$C(=O)], wherein n is an integer between 0-20; and
  (vi) m is 0 when X is [(CH$_2$CH$_2$O)$_{n'}$(CH$_2$)$_{q'}$C(=O)], wherein n' is an integer between 0-10,000 and q' is an integer between 2-4.

In another aspect, the invention features a compound having a structure according to the following formula,

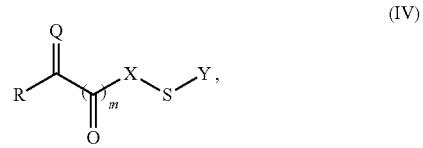

(IV)

where

R is H, optionally substituted $C_{1-20}$ alkyl, optionally substituted $C_{2-20}$ alkynyl, optionally substituted $C_{6-14}$ aryl, or optionally substituted 5-14 membered heteroaryl;

Q is O or W(O)$_{p1}$(CH$_2$)$_q$(O)$_{p2}$-L;

W is N, NNH, or NNHCO;

each of p1 and p2 is, independently, 0 or 1;

q is an integer between 1-20;

L is —N=(Bio), —NHN=(Bio), CONHN=(Bio), NH-(Bio), NHNH-(Bio), where Bio is a biologically active agent covalently attached to nitrogen via a single or double bond as shown;

Y is optionally substituted $C_{1-20}$ alkyl or optionally substituted $C_{6-14}$ aryl; and wherein m and X are defined as follows, wherein
  (i) m is 1 when X is —[NHCH(R')C(=O)]$_n$, wherein n is an integer between 0-20 and R' is the side chain of any natural or unnatural α-amino acid;
  (ii) m is 1 when X is [NH(CH$_2$)$_n$C(=O)], wherein n is an integer between 0 and 20;
  (iii) m is 1 when X is [NZ(CH$_2$CH$_2$O)$_{n'}$(CH$_2$)$_{q'}$(=O)], wherein Z is H or optionally substituted $C_{1-20}$ alkyl, n' is an integer between 0-10,000, and q' is an integer between 2-4;
  (iv) m is 0 when X is [(CH$_2$)$_q$\{NCH(R')C(=O)\}$_n$], wherein q is an integer between 1-20, n is an integer between 0-20, and R' is the side chain of any natural or unnatural α-amino acid;
  (v) m is 0 when X is [(CH$_2$)$_n$C(=O)], wherein n is an integer between 0-20; and
  (vi) m is 0 when X is [(CH$_2$CH$_2$O)$_{n'}$(CH$_2$)$_{q'}$C(=O)], wherein n' is an integer between 0-10,000 and q' is an integer between 2-4.

In some embodiments, Bio is selected from a pharmaceutical, an imaging moiety, or an antibody.

In other embodiments, Q is O.

In still other embodiments, Q is W(O)$_{p1}$(CH$_2$)$_q$(O)$_{p2}$-L.

In another aspect, the invention features a method of covalently attaching proteins to a protein or a biologically active agent that includes
  (a) combining a first protein with a second reagent selected from biologically active agent or a protein;
  (b) forming a covalent attachment between said first protein and said biologically active agent or second protein, where the covalent attachment is formed via a reversible reaction; and (c) subsequently forming a second covalent attachment between said first protein and said biologically active agent or second protein, where the covalent attachment is formed via an irreversible reaction.

In some embodiments, the reversible reaction of step (b) comprises a reaction between a reagent that includes a linker group having bisaminoxy, bis-hydrazine, or bis-semicarbazide functionality, or any combination thereof, and (i) said first protein that includes a ketone or aldehyde group, and/or (ii) said second reagent that includes a ketone or aldehyde group.

In other embodiments, the reversible reaction of step (b) includes a reaction between a reagent having a linker group comprising two carbonyl groups selected from aldo- or keto-groups, and (i) the first protein that includes a bisaminoxy, bis-hydrazine, or bis-semicarbazide functionality, and/or (ii) the second reagent that includes a bisaminoxy, bis-hydrazine, or bis-semicarbazide functionality, or any combination thereof.

In some embodiments, the irreversible reaction of step (c) includes a cycloaddition reaction. In further embodiments, the cycloaddition reaction includes an alkynyl component and an azido component, or a diene component and a dienophile component.

In some embodiments, the method includes a first protein having a structure according to the formula

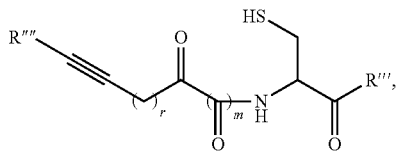

where R'" is a protein, R"" is H, optionally substituted $C_s$ alkyl, optionally substituted $C_{6-12}$ aryl, or an optionally substituted 5-14 membered heteroaryl, r is an integer between 6-18, m is 0 or 1, where s is an integer between 1 and 18, and wherein (r+s) is ≤20; and a second reagent having a structure according to the formula

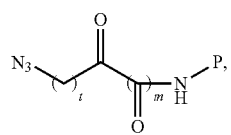

where t is an integer between 6-20, m is 0 or 1, and P is a protein.

In other embodiments, the reversible reaction of step (b) includes a reaction where the first protein includes a thiol.

In other embodiments, the reversible reaction of step (b) includes disulfide bond formation.

In certain embodiments, the irreversible reaction of step (c) comprises a cycloaddition reaction. In further embodiments, the cycloaddition reaction includes an alkynyl component and an azido component, or a diene component and a dienophile component.

In some embodiments, the first protein has a structure according to the formula

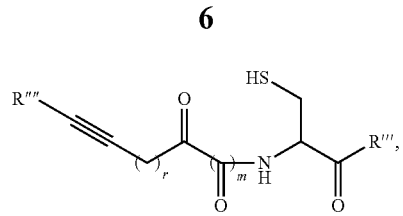

wherein R'" is a protein, R"" is H, optionally substituted $C_s$ alkyl, optionally substituted $C_{6-12}$ aryl, or an optionally substituted 5-14 membered heteroaryl, r is an integer between 6-18, m is 0 or 1, where s is an integer between 1 and 18, and where (r+s) is ≤20; and a second reagent having a structure according to the formula

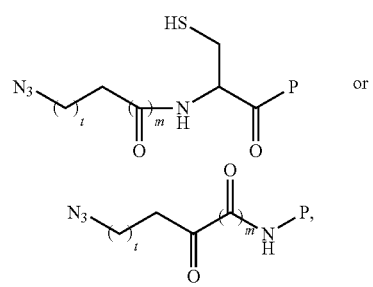

where t is an integer between 5-20, P is a protein, and m is 0 or 1.

In another aspect, the invention features a compound having the following structure,

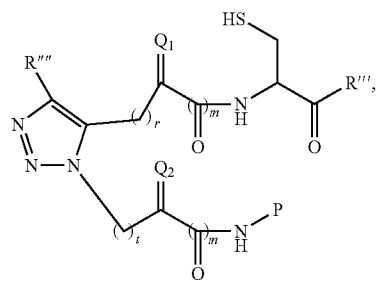

where
R'" is a protein,
R"" is H, optionally substituted $C_s$ alkyl, optionally substituted $C_{6-12}$ aryl, or an optionally substituted 5-14 membered heteroaryl,
r is an integer between 6-18,
each m is, independently, 0 or 1,
s is an integer between 1 and 18, where (r+s) is ≤20;
t is an integer between 6-20,
P is a protein; and
$Q_1$ and $Q_2$ are both O, or $Q_1$ and $Q_2$ combine to form a linker having the structure NX-L-NX, where each X is O, NR', or NR'C(=O), R' is H, optionally substituted $C_{1-20}$ alkyl, or optionally substituted $C_{6-14}$ aryl; and L is selected from (i) $(CH_2)_n$, where n is an integer between 1-1000;
(ii) $(CH_2CH_2O)_nCH_2CH_2$, where n is an integer between 1-1000; and
(iii) a peptide chain that includes 3-25 amino acids.

In another aspect, the invention features a compound having the following structure,

[chemical structure]

where
R''' is a protein,
R'''' is H, optionally substituted $C_s$ alkyl, optionally substituted $C_{6-12}$ aryl, or an optionally substituted 5-14 membered heteroaryl,
r is an integer between 6-18,
m is 0 or 1,
s is an integer between 1 and 18, wherein (r+s) is ≤20;
t is an integer between 5-20;
P is a protein; and
each $R_x$ is H, or both $R_x$ combine to form a disulfide bond.

In another aspect, the invention features a compound having the following structure,

[chemical structure] (X)

where
P is a protein;
X is O, NR', or NR'C(=O);
R' is H, optionally substituted $C_{1-20}$ alkyl, or optionally substituted $C_{6-14}$ aryl; and
L is (i) $(CH_2CH_2O)_nCH_2CH_2$, wherein n is an integer between 1-1000; or (ii) a peptide chain that includes 3-25 amino acids.

In still another aspect, the invention features a method of site specifically producing a multimeric protein that includes combining a multifunctional linker and one or more proteins, where the multifunctional linker can form a covalent attachment to the protein.

In some embodiments, the multimeric protein is a dimer, where the method further includes a bifunctional linker; a trimer, where the method further includes a trifunctional linker; or a tetramer, where the method further includes a tetrafunctional linker.

In some embodiments, the protein self-dimerizes or self-aggregates in a non-covalent manner, for example, even at high dilution. In further embodiments, the protein is a four helix bundle protein or includes a zipper binding motif. In some embodiments, the protein is a cytokine (e.g., a long chain cytokine).

In other embodiments, the multimer is a dimer. In further embodiments, the dimer is an immunoconjugate. In still further embodiments, the immunoconjugate includes an intact antibody fragment, a single-chain variable fragment (scFv), a diabody, a minibody, or a scFv-Fc fragment.

In some embodiments, the protein includes an amino acid residue having an aldo- or keto-functional group.

In certain embodiments, the amino acid residue is the N-terminal amino acid.

In other embodiments, the amino acid residue is a surface available residue.

In some embodiments, the aldo- or keto-functional group is an α-carbonyl functional group.

In further embodiments, the multifunctional linker is a bifunctional linker including a functional group that is aminooxy, hydrazine, or semicarbazide. For example, the bifunctional linker is a bis-aminooxyalkane $NH_2O(CH_2)_nONH_2$ where n is an integer between 1-20; a bis-hydrazino-alkane $NH_2NH(CH_2)_nONHNH_2$ where n is an integer between 1-20; a bis-semicarbazide-alkane $NH_2NRCO(CH_2)_nOCNRNH_2$ where n is an integer between 1-20; or the bifunctional linker includes a 1,ω-substituted polyethylene glycol polymer including up to 1000 monomeric moieties.

In some embodiments, the protein includes a glycine or alanine residue at the N-terminus. In further embodiments, the multi-functional linker is a bis-anhydride, bis-imidate, bis-carbonyl imidazole, or a heterobifunctional reagent.

In some embodiments, the protein includes a thiol function group at the N-terminus. In further embodiments, the bifunctional linker is a 1,ω-bismaleimide alkane having the structure $X—(CH_2)_n—X$, where X is N-maleimide and n is an integer between 1-20. In other embodiments, the bifunctional linker includes a 1,ω-substituted polyethylene glycol polymer including up to 1000 monomeric moieties.

In some embodiments, the protein includes two amino acid residues that have an aminooxy, a hydrazine, or a semicarbazide -functional group, or any combination thereof. In other embodiments, the bifunctional linker includes aldo- or keto-functional groups, or a combination thereof.

In some embodiments, the proteins further include functional groups that can form a covalent linkage to a second protein via an irreversible reaction. In other embodiments, the irreversible reaction is a cycloaddition reaction. In further embodiments, the cycloaddition reaction includes an alkynyl component and an azido component, or a diene component and a dienophile component.

In another aspect, the invention features a compound having the following structure,

[chemical structure]

where
R is H, optionally substituted $C_{1-20}$ alkyl, optionally substituted $C_{2-20}$ alkynyl, optionally substituted $C_{6-14}$ aryl, or optionally substituted 5-14 membered heteroaryl;
L is
(i) $(CH_2)_{q1}$, where q1 is an integer between 1-20;
(ii) $(CH_2CH_2O)_{q2}CH_2CH_2$, where q2 is an integer between 1-1000; or
(iii) a peptide chain including 3-25 amino acids;
$W_1$ is N, NNH, or NNHCO;
$W_2$ is $NH_2$, $NHNH_2$, or $NHNH_2CO$ each of p1 and p2 is, independently, 0 or 1; and Bio is a therapeutic agent or a diagnostic agent.

In another aspect, the invention features a method of functionalizing a protein including combining the compound having the structure

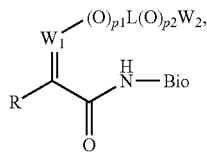

described herein, with the protein, where the protein includes an α-carbonyl functional group.

In another aspect, the invention features a compound having the following structure,

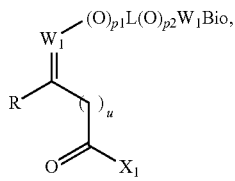

where

R is H, optionally substituted $C_{1-20}$ alkyl, optionally substituted $C_{2-20}$ alkynyl, optionally substituted $C_{6-14}$ aryl, or optionally substituted 5-14 membered heteroaryl;

L is (i) $(CH_2)_{q1}$, where q1 is an integer between 1-20;
(ii) $(CH_2CH_2O)_{q2}CH_2CH_2$, where q2 is an integer between 1-1000; or
(iii) a peptide chain including 3-25 amino acids each $W_1$ is N, NNH, or NNHCO;

each of p1 and p2 is, independently, 0 or 1;

u is an integer between 0-20;

Bio is a therapeutic agent or a diagnostic agent; and $X_1$ is halogen, or $OR_y$, where $R_y$ is H, optionally substituted $C_{1-20}$ alkyl, optionally substituted $C_{2-20}$ alkynyl, or optionally substituted $C_{6-14}$ aryl.

In another aspect, the invention features a method of functionalizing a protein including combining the compound having the following structure,

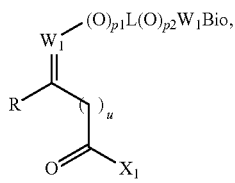

as described herein, with the protein.

In still another aspect, the invention features a method of labeling a protein including a thiol function group, the method including (a) combining the protein with 3-bromopyruvate; and (b) treating the product with a reagent including a linker group including bisaminoxy, bis-hydrazine, or bis-semicarbazide functionality, and further including a biologically active agent.

In another aspect, the invention features a method of forming a covalent bond between two functional groups (e.g., two carbonyl groups) in a protein including treating the protein with a bifunctional linker.

In some embodiments, the protein includes two carbonyl groups selected, independently, from an aldo- and a keto-group. In further embodiments, one of the carbonyl groups is derived from an amino acid selected from the group consisting of

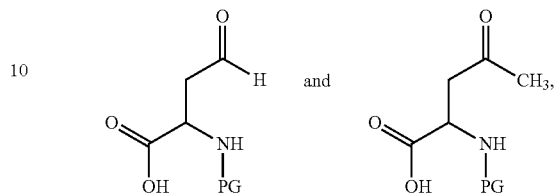

where PG is H or an N-protecting group. In still other embodiments, one of the carbonyl groups is introduced by a transamination reaction. In some embodiments, the bifunctional linker includes a functional group that is aminooxy, hydrazine, or semicarbazide. In some embodiments, the bifunctional linker is a bis-aminooxyalkane $NH_2O(CH_2)_nONH_2$ where n is an integer between 1-20; a bis-hydrazino-alkane $NH_2NH(CH_2)_nONHNH_2$ where n is an integer between 1-20; a bis-semicarbazide-alkane $NH_2NRCO(CH_2)_nOCNRNH_2$ where n is an integer between 1-20; or includes a 1, ω-substituted polyethylene glycol polymer having 1-1000 monomeric moieties. In still further embodiments, the crosslinking reactions are catalyzed by amine enhancers (Dirksen et al., *Bioconjug. Chem.* 19:2543-8, 2008).

In some embodiments, the protein includes two amino acid residues including aminooxy groups. In certain embodiments, the amino acid residues are derived from the following structures,

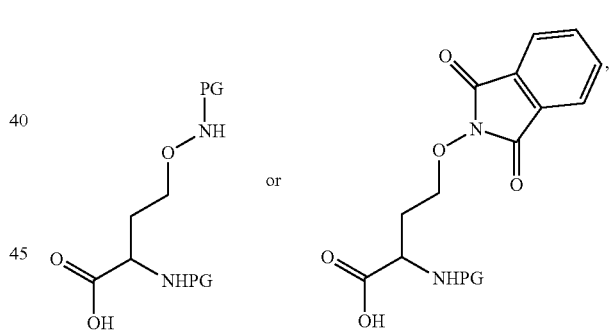

where PG is H or an N-protecting group. In further embodiments, the bifunctional linker has a structure according to $RC(=O)—(CH_2)_n—C(=O)R$, where n is an integer from 1-20, and each R is, independently, optionally substituted $C_{1-20}$ alkyl, optionally substituted $C_{2-20}$ alkynyl, optionally substituted $C_{6-14}$ aryl, or optionally substituted 5-14 membered heteroaryl.

In other embodiments, the protein includes two amino acid residues including thiol groups. In further embodiments, the bifunctional linker has a structure according to $XCH_2C(=O)—(CH_2)_n—C(=O)CH_2X$, where X is a halogen.

The term "alpha nucleophile" includes a nucleophile bearing an unshared pair of electrons on an atom adjacent to the nucleophilic site.

The term "A-leptin" is used to describe a leptin that includes an alanine residue at the N-terminus. For example, an A-leptin can be a Leptin Human Recombinant Protein sold by Prospec Protein Specialists, Rehovot Science Park, PO.

Box 398 Rehovot 76103, Israel, where the first five N-terminal amino acids have the sequence Ala-Val-Pro-Ile-Gln.

The terms "ω-aldoacyl" or "ω-ketoacyl-thioester" refer to 2-oxacyl moieties that are linked by a chain of atoms to a thioester moiety at the opposite end of the chain.

The terms "alkoxyl amine" and "aminooxy group" are used interchangeably herein and generally describe a species containing the moiety, —CH$_2$ONH$_2$.

The term "α-carbonyl amide" is meant to describe an α-ketoamide or an α-aldoamide.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2- dimethylpentyl, 2,3-dimethylpentyl, n-heptyl, n-octyl, n-nonyl, n-decyl and the like. Furthermore, the expression "C$_x$-C$_y$-alkyl", wherein x is 1-5 and y is 2-10 indicates a particular alkyl group (straight- or branched-chain) of a particular range of carbons. For example, the expression C$_1$-C$_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., C$_2$-C$_6$ for straight chain, C$_3$-C$_6$ for branched chain). The term C$_2$-C$_6$ includes alkynyl groups containing 2 to 6 carbon atoms.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term cycloaddition refers to a pericyclic chemical reaction, in which two or more unsaturated molecules (or parts of the same molecule) combine with the formation of a cyclic adduct in which there is a net reduction of the bond multiplicity.

The term "fusion protein" includes a single molecular entity having at least two polypeptide domains that are not normally present in a single, natural polypeptide. Thus, naturally occurring proteins are not "fusion proteins", as used herein.

The term "heteroaryl," as used herein, represents an aromatic (i.e., containing 4n+2 pi electrons within the ring system) mono-, bi-, or tricyclic-membered ring having between 5-14 ring members and containing one, two, three, or four heteroatoms independently selected from the group consisting of nitrogen, oxygen, and sulfur. Exemplary heteroaryls include, but are not limited to pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl (e.g., 1,3, 4-thiadiazole), isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "2-iminoacyl" or "α-iminoacyl" is meant to indicate the direct attachment of an imino moiety at the imino carbon to a carbonyl either of an aldehyde or a ketone.

The term "2-oxacyl" or "α-oxacyl" is meant to indicate two carbonyls that are directly attached to each other, one being either an aldehyde carbonyl or a keto carbonyl.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, arthritis, atherothrombosis, plaque rupture, or Crohn's disease. In another embodiment, the subject is a cell.

The term "peptide" includes chains of amino acids linked by peptide bonds. The term "peptide" can also refer to a "protein" or "polypeptide" (e.g., annexin proteins, granulocyte macrophage colony-stimulating factor, human superoxide dismutase, leptin, myoglobin, albumin, avidin, and an enzyme), which are compounds made of amino acids arranged in a linear chain and folded into a globular form. A variety of polypeptides or proteins may be used within the scope of the methods and compositions provided herein. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the common amino acids found in naturally occurring proteins, or at least one modified or unusual amino acid. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The protein, polypeptide and peptide sequences can be found at computerized databases known to those of ordinary skill in the art. One such database is the National Center for Biotechnology Information's Genbank and GenPept databases. Alternatively, various commercial preparations of proteins, polypeptides, and peptides are known to those of skill in the art.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, halogen (—F, —Cl, —Br, or —I), azido (—N$_3$), nitro (—NO$_2$), cyano (—CN), acyloxy (—OC(=O)R'), acyl (—C(=O)R'), alkoxy (—OR'), amido (—NR'C(=O)R" or —C(=O)NRR'), amino (—NRR'), carboxylic acid (—CO$_2$H), carboxylic ester (—CO$_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl. In some embodiments, the substituent groups themselves may be further substituted with, for example, 1, 2, 3, 4, 5, or 6 substituents as defined herein. For example, a $C_{1-6}$ alkyl, phenyl, or heteroaryl group may be further substituted with 1, 2, 3, 4, 5, or 6 substituents as described herein.

The present invention includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The present invention includes all pharmaceutically acceptable isotopically-labeled compounds of the invention, wherein one or more atoms are replaced by atoms having the same atomic number, but an atomic mass or mass number different from the atomic mass or mass number usually found in nature. Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

DETAILED DESCRIPTION OF THE INVENTION

The present invention generally relates to chemical ligation to substrates that include 2-aminothiol moieties, a moiety exemplified by terminal cysteine residues. The present invention also generally relates to site-specific modifications of proteins at their N-termini that include 2-aminothiol moieties. The present invention also relates to chemical modification of proteins at their N-termini via chemical ligation that introduces oxacyl, iminoacyl analogs (e.g., 2-oxacyl or 2-iminoacyl), or single carbonyls, in order to attach various biologically active agents through corresponding oxime, hydrazone, and semicarbazone linkages in a subsequent step. Further, the present invention generally provides methods for the site-specific modification of peptides, polypeptides, and proteins at their N-termini or at protein surfaces (e.g., via certain unnatural amino acids introduced along the peptide framework).

The present invention further relates to methods of making and using such adducts in radio-labeling, molecular imaging and protein therapeutic applications, and the treatment of disorders such as cancer, Crohn's disease, atherothrombosis, arthritis, and plaque rupture.

Orthogonal Conjugative Reactions for Protein Conjugation

Scheme 1 shows three distinct categories of reaction that have been developed to forge, chemospecifically, covalent bonds to proteins in order to prepare conjugates. These reactions are regarded to be orthogonal to those in which peptides normally participate (in Scheme 1, P=protein, polypeptide or peptide). These strategies can be used in the synthetic methods described herein for the site specification functionalization

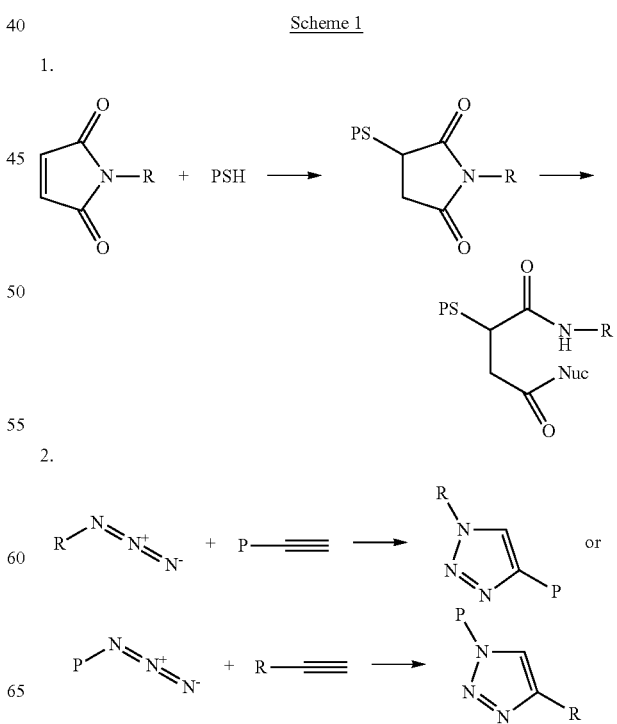

3.

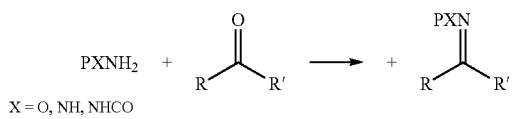

X = O, NH, NHCO

Thiol Addition Reaction

Exemplary thiol reactions that are orthogonal to classic peptide reactions include Michael additions to N-substituted maleimides. These reactions can be slow with proteins, requiring incubation of maleimide at high concentrations over several hours and are often incomplete. Further, the resulting succinimide adducts are subject to (nucleophilic) reactions at the imide carbonyl moieties that can give rise to undesirable heterogeneities or produce epimers.

Dipolar Addition Reactions

A second category of orthogonal reactions includes Huisgen 1,3-dipolar additions of acetylenes to azides, a transformation that is regarded as the examplar of "click chemistry." The facility with which this reaction proceeds, however, is dependent upon a number of factors that impact its rate. For example, the chemistry generally requires the addition of cupric salts to be practical. The use of cupric salts in conjunction with the synthesis of protein conjugates is somewhat limiting because of its potential toxicity, interferences with other metals bound by the native protein, and the difficulties associated with manufacturing. Catalysis of this reaction has also been described using the enzyme acetylcholinesterase as a template: when this enzyme is incubated with libraries of acetylenes and azides, cycloaddition is catalyzed by binding complementary entities in appropriate apposition for reaction.

Carbonyl Addition and Condensation Reactions

A third category is exemplified by carbonyl reactions of aminooxy and hydrazine functions (for a general discussion, see Kalia et al., *Angewandte Chemie International Edition*, 7633-7636, 2008). Reactions with carbonyl reagents can be quite facile and catalysis can provide product quantitatively within minutes. The reversibility of oxime and hydrazone formation, however, can be a potential limitation for conjugates requiring extended duration. Further, and in contrast to conjugations that exploit either native cysteines or recombinantly expressed cysteines, protein based keto- or aldogroups are less synthetically accessible.

The N-terminal Amino Group as a Target for Protein Conjugation

The N-terminal amino group of proteins is a distinctive feature, common to virtually all proteins, that has been singled out for protein modification. Because it is alpha to an acyl function, its pKa is lower than that of primary amines (e.g., those present in lysine side chains, which lack such alpha substituents). The pKa difference therefore provides a convenient basis for selective modification of the N-terminal residue by electron-deficient substrates. Nonetheless, the lone N-terminal amino group must compete not only with multiple lysines that combine for a statistical effect, but also the altered reactivities of lysines and other protein nucleophilic residues that may be modified by local interactions (e.g., relay systems and nearest neighbor interactions). For proteins possessing only a few lysines, e.g. insulin, selectivity may be marked, but high selectivity is difficult to achieve for polypeptides containing diverse, multiple lysine residues and is generally not successful. To be compelling, claims to that effect must pass the rigorouss test of significant coverage by mass spectroscopy of peptide lysates.

The α-hydrogen of the N-terminal amino acid residue of protein also represents a unique point of attack that has been exploited in transamination reactions of certain proteins. Imine formation, as described in Scheme 2, activates the α-proton which can then be translocated across the aza-allylic system, giving rise to carbonyl-imine (2). The latter species can be subsequently hydrolyzed to the α-carbonyl amide (3).

Scheme 2

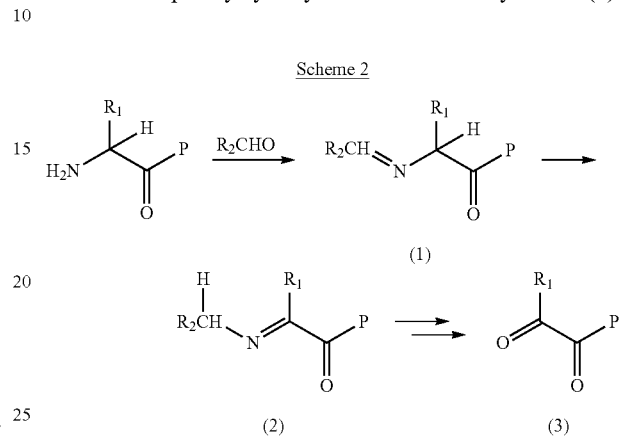

N-terminal modification of certain peptides using transamination reactions has been reported (e.g., Dixon, *Journal of Protein Chemistry*, 3:99-108, 1984, and references therein). Dixon describes transamination reactions that occur within a pH range of 5-7, are specific for N-terminal amines of αamino groups and can be used for removal of N-terminal residues of proteins under non-denaturing conditions. For example, see Sunde et al., *Biochim. Biophys. Acta* 1388:45-52, 1998). Other examples of converting human growth hormone to the corresponding terminal α keto-amide have been cited (e.g., Nishimura et al., *Chem. Commun.* 1135-1136, 1998; Gilmore et al., *Angew. Chem. Int. Ed.* 45:5307-5311, 2006; and Christman et al. *J. Mat. Chem.* 17:2021-1627, 2007).

These transamination methods may have certain challenges. For example, the methods employ harsh reaction conditions under which it is difficult to maintain the folded structure of proteins necessary for their activity. The methods can result in side reactions that make it difficult to control or limit the reaction to the N-terminal of target proteins. Further, the methods are not generally applicable to a broad range of proteins: they can be (unpredictably) successful only with a narrow subset of proteins, thereby severely limiting the scope of these methods. The transamination reaction usually requires overnight incubations at high concentrations of the transaminating agent in order to obtain substantial conversions to the desired α-carbonyl amide.

Chemical Ligation of Aldo-, Keto-, and α-Carbonyl Groups to Proteins and Polypeptides In view of the limitations of transamination methods as routes to commercially viable conjugates, it would be useful to develop additional methods for attaching α-carbonyl species (2-oxacyl moieties) directly to the protein target. Described herein are methods (Scheme 3) by which α-carbonyl moieties can be attached irreversibly to proteins, either via substrates in which the 2-oxacyl moiety is directly linked to the thioester (X=zero, Scheme 3) or, alternatively, via substrates in which the 2-oxacyl moiety is separated from the thioester function by a linker exemplified by Compounds 4 a-c.

Scheme 3

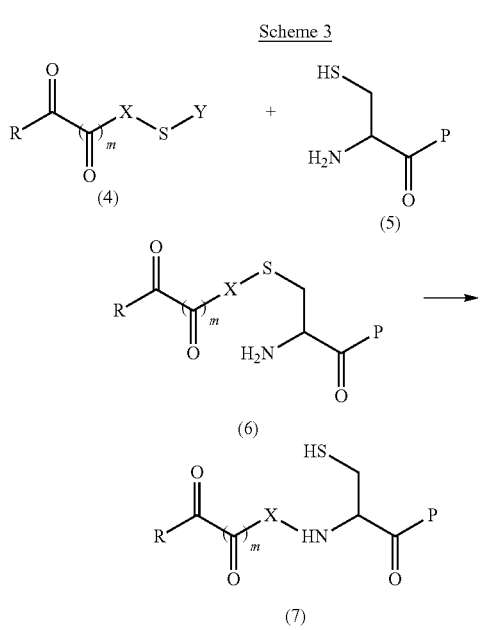

Y = aryl or alkyl as normally employed in native chemical ligation

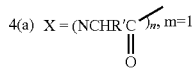

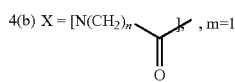

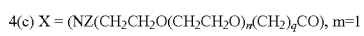

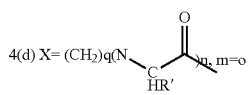

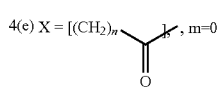

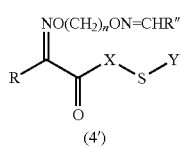

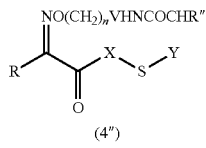

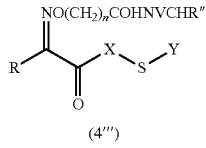

V=O, CH$_2$

Bifunctional Linkers

A variety of linkers can be envisaged including non-nucleophilic amino acid or peptide functionality (4(a) in which R' can be independently varied for each residue, n is an integer between 1-20), ω-aminoacids, n is an integer between 1-20 (4(b)), and PEG linkers such as 4(c) (n=1-1000), and the like.

Peptide and Protein Starting Materials having Terminal Cysteines

As shown herein in Scheme 3, α-carbonyl thioesters (4, X=zero), or thioesters connected by a linker to 2-oxacyl groups (4a-c), can be
 (1) directly attached to polypeptides or proteins which occur naturally with N-terminal cysteines;
 (2) engineered with N-terminal cysteines by recombinant methods; or
 (3) be prepared synthetically bearing β-aminothiol entities.
Since most proteins that are used intensively in research are now cloned and expressed, polypeptides or proteins that possess cysteine extensions at their N-termini are generally accessible (Gentle et al., *Bioconjug Chem.* 15: 658-63, 2004, and Hauser et al., *Protein Expr Purif.* 54:227-33, 2007).

Synthesis of Compounds 4

The methods we describe for ligation of 2-oxacyl moieties have the advantage of producing α-carbonyl amides much more rapidly than current methods. The latter tend to be time-consuming and labor intensive and involve the harsh treatment of proteins with huge excesses of transaminating reagents. With the availability of pyruvyl and glyoxyl precursors (see, e.g., Ottenheijm et al., *Synthesis*, 467-469, 1996), a strategy for attachment of 2-oxacyl moieties can be founded on native chemical ligation to peptide or proteins by exploiting the presence of cysteines at N-termini. Further, an analogous strategy can be implemented for the corresponding imino substrates (4'), (4"), and (4"'), for which biologically active agents and linkers can be constructed before attachment to the protein in a final step. This method can be useful in avoiding further organic chemical modifications in aqueous media once the system has been assembled: Additional variants of this strategy can employ hydrazines and hydrazides moieties in lieu of aminooxy groups to establish linkages.

Since it is the α-carbonyl of the α-carbonyl amide that is the reactive function for the carbonyl reagents exemplified by alkoxyl amines that carry biologically active agents, keto- and aldo-thioester substrates lacking the amido group (4, m=0) are also shown to serve as targets of these carbonyl reagents. Accordingly, an entirely analogous series is shown for the simple aldehyde and ketone series 4(d)-(f). Synthetic routes to the ultimate thioester reagents 4(a)-(c) are available using commercially available starting materials that can then be activated for attachment of 2-oxacyl moieties to the linker nitrogen. For example, α-carbonyl species such as pyruvic acid can be activated to acylate acceptor amines in a variety of ways: in the form of potent electrophiles such as acid chlorides to more subtly reactive species, e.g, "active esters," spanning the gamut of oxygen and thioesters known in the art.

The same driving forces that have proved effective in native and expressed chemical ligations with simple thioesters (e.g., Johnson et al., *J. Am. Chem. Soc.* 128: 6640-6646, 2006, and Kent, *Chem. Soc. Rev.* 38:338-351, 2009) are operative for α-carbonyl thioesters represented in Scheme 3. The α-aldo- or keto-group itself represents a potential point of attack by lysines and other protein nucleophiles that could in some instances result in reactions other than acylation of the N-terminal group. Undesirable secondary reactions may be avoided by isolating the 2-oxacyl function from the thioester moiety by a peptide linker (or other functionality) as the less reactive α-carbonyl amide, thus placing the reactive thioester component at the other end of the molecule.

In instances in which the presence of α-carbonyl functionality might complicate the execution of subsequent synthetic modifications, the corresponding α-oximinoether-thioesters (13), prepared by either standard solution phase, or solid phase routes (Scheme 4), can serve as the cysteine-reactive component. In this Scheme, the entity Y to be conjugated to the protein can be introduced through the α-oximino thioester (13). This strategy allows for the introduction of functionality that cannot easily be reduced, protected, or freed, when linked to the protein. Although Scheme 4 shows the thioester (13) as being generated directly from solid phase carbonyl substrates (12), alternate paths to acyl transfer agents are available. Free carboxylic acids corresponding to (12) can mediate thioester formation by standard procedures in solution; resin-bound acylureas can also mediate the formation of thioesters and acyl transfers in situ (see, e.g., Blanco-Canosa et al., *Angew. Chem. Int. Ed.* 47:6851-6855, 2008).

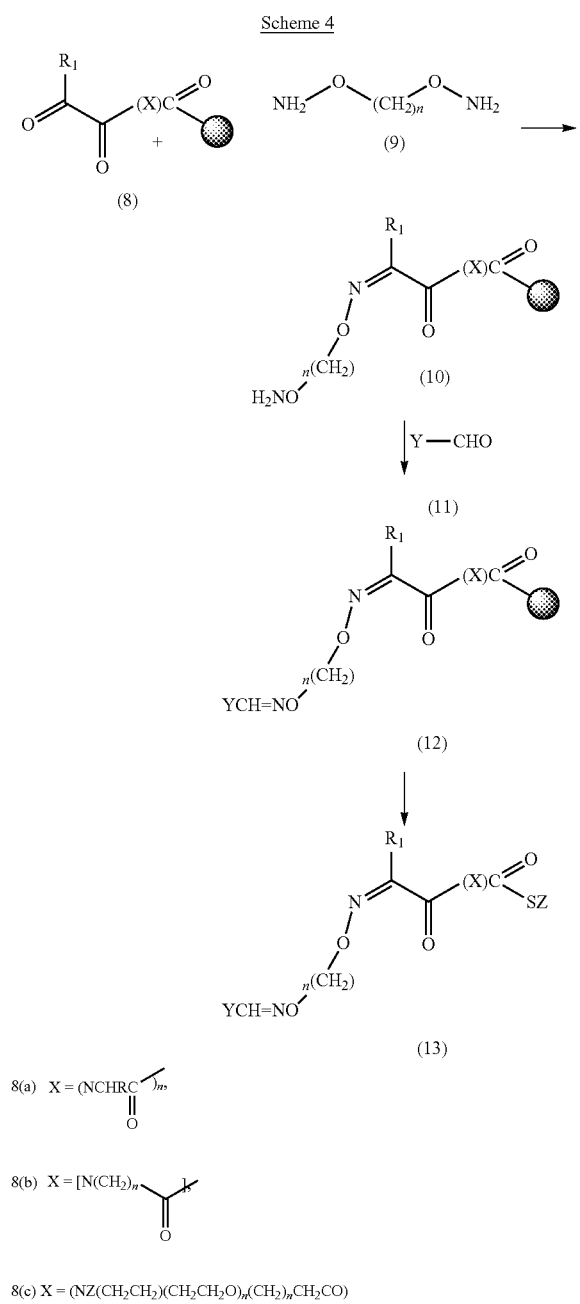

and aldehyde functions to protein targets. A variety of commercially available substrates, such as keto acids $CH_3CO(CH_2)_nCOOH$ (n=1-3), can be transformed by methods known in the art to the corresponding thioesters. Similarly, more complex keto acids and longer chain keto acids can be prepared by those skilled in the art using standard and established protocols. Accordingly, there are numerous thioester substrates available for use in the methods described herein for functionalizing terminal cysteine residues.

Chemistry of Carbonyl Species

The introduction of carbonyl moieties by site-specific modification of cysteine residues expands the repertoire of reactions available to proteins to include the many examples of carbonyl reactions (e.g., *Chemistry of the Carbonyl Group* (Chemistry of Functional Groups) Saul Patai (Editor), John Wiley & Sons Ltd., 1966)). Exemplary reactions therefore include aldol condensations, multicomponent reactions (e.g., Mannich reactions), and Wittig reactions, although the latter reaction has been of limited utility in aqueous media to date. Accordingly, many carbonyl condensation reactions are potential vehicles for the introduction of a variety of ligands and useful extensions of the main chain protein.

Facilitating Irreversible Reactions Through Proximity Effects Imposed by Reversible Reactions Chemical ligation of 2-oxacyl species to proteins can be adapted to promote irreversible reactions that are slow in aqueous media and require long reaction times without the benefit of catalysis. For example, although click chemistry (Kolb et al., *Angewandte Chemie International Edition* 40(11): 2004-2021) has been utilized to unite peptide components irreversibly, copper salts are required to produce adducts within reasonable reaction times, a strategy that has certain limitations (vide supra). Irreversible reactions are required for applications in which covalency must be sustained over long periods, e.g., to increase the duration of action of protein therapeutics. Carbonyl adducts of ketones and aldehydes may not have the requisite stability for the duration of action required for therapeutics (Kalia et al., vide supra). Therefore a rapid and efficient method that can effect, e.g., 1,3-dipolar additions between acetylenes and azides in aqueous media and free of metals, would represent a significant advance in the application of click chemistry to the production of protein conjugates.

The use of the enzyme acetylcholinesterase as a template to bring separate acetylenic and azide components together and pre-organize them for a facile reaction, exploits proximity effects (Radio et al., *Chem Biol Interact.* 175, 161-5, 2008). In the methods described herein, these components can be brought together in a different way by employing the rapid and reversible condensation reactions of ketones and aldehydes with alkoxyl amines in combination with the irreversible 1,3-dipolar additions of acetylene with azides, which occur slowly in the absence of metal catalysis (Scheme 5). Since the carbonyl-oxime pair reacts independently and much more rapidly than the acetylene-azide pair, a mechanism is available for facilitating the 1,3-dipolar addition reaction through proximity effects.

Scheme 5
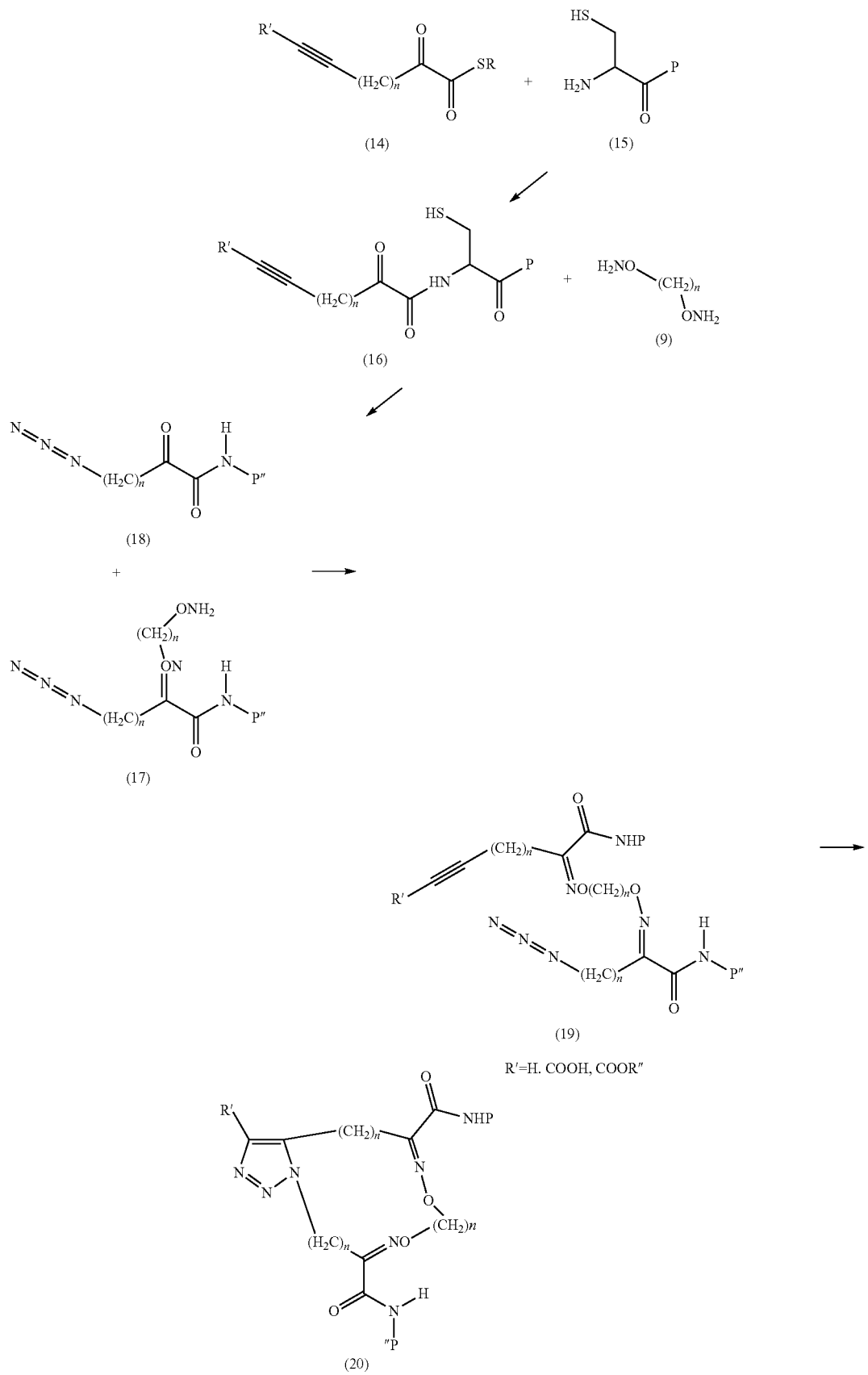

As shown in Scheme 5, the introduction of α-carbonyl species onto protein frameworks through ligation or transamination provides a means of bringing poorly reactive entities at ambient and physiological temperatures together in close proximity. In this manner, the chemical reactivity is augmented through entropy effects. This is accomplished by exploiting the relatively rapid, but potentially reversible formation of oximes or other like doubly-bonded entities. The condensation of the bis-aminooxy reagents (9) with the α-keto group of (16), creates an intermediary protein-monooxime containing a primary aminooxy function as well (17) that is available for further coupling. The acetylenic moiety in (17) can then be contacted with an azide (18) in a further step to unite the components of the 1,3-dipolar addition in (19) giving triazole product (20). Thus, by incorporating the acetylene and azide in separate components, and then bringing them together in a relatively rapid reaction, a facile path is created for a rapid intramolecular reaction between the acetylenic and azide components. Analogous to the primary reactions involving oxime formation, hydrazone formation can be used to as a vehicle to promote 1,3-dipolar additions. Note that in Scheme 5, the roles of (16) and (18) as mediators of mono-oxime formation en route to (20) can be reversed.

The acetylene/azide coupling can also be effected through paths involving thiol-disulfide exchange as portrayed in Scheme 6.

This principle for accelerating reactions can be applied to a number of cycloaddition reactions. Representative cycloaddition reactions include the reaction of an alkene with a 1,3-diene (Diels-Alder reaction) and the reaction of an alkene with an α,β-unsaturated carbonyl (hetero Diels-Alder reaction). Selected, non-limiting examples of moieties that serve as components of cycloaddition reactions are: alkenes, alkynes, carbonyl groups, imine groups, 1,3-dienes, α,β-unsaturated carbonyls, and azides.

Accordingly, this approach constitutes a general method for accelerating the conjugation or fusing together of proteins and other macromolecules. First, relatively fast reversible reactions are employed to link the initially, separate, slower reactive, components together. Secondly, the slower reactive components, are enabled, by virtue of their proximity and orientation, to undergo an irreversible intramolecular reaction Intramolecular Covalent Bond Formation The above approaches show that proteins can be covalently tethered using a sequence that includes a first reversible reaction and a second irreversible reaction. Intramolecular tethering can also be accomplished by employing functional groups found within a single protein structure and a bifunctional linker (Scheme 7).

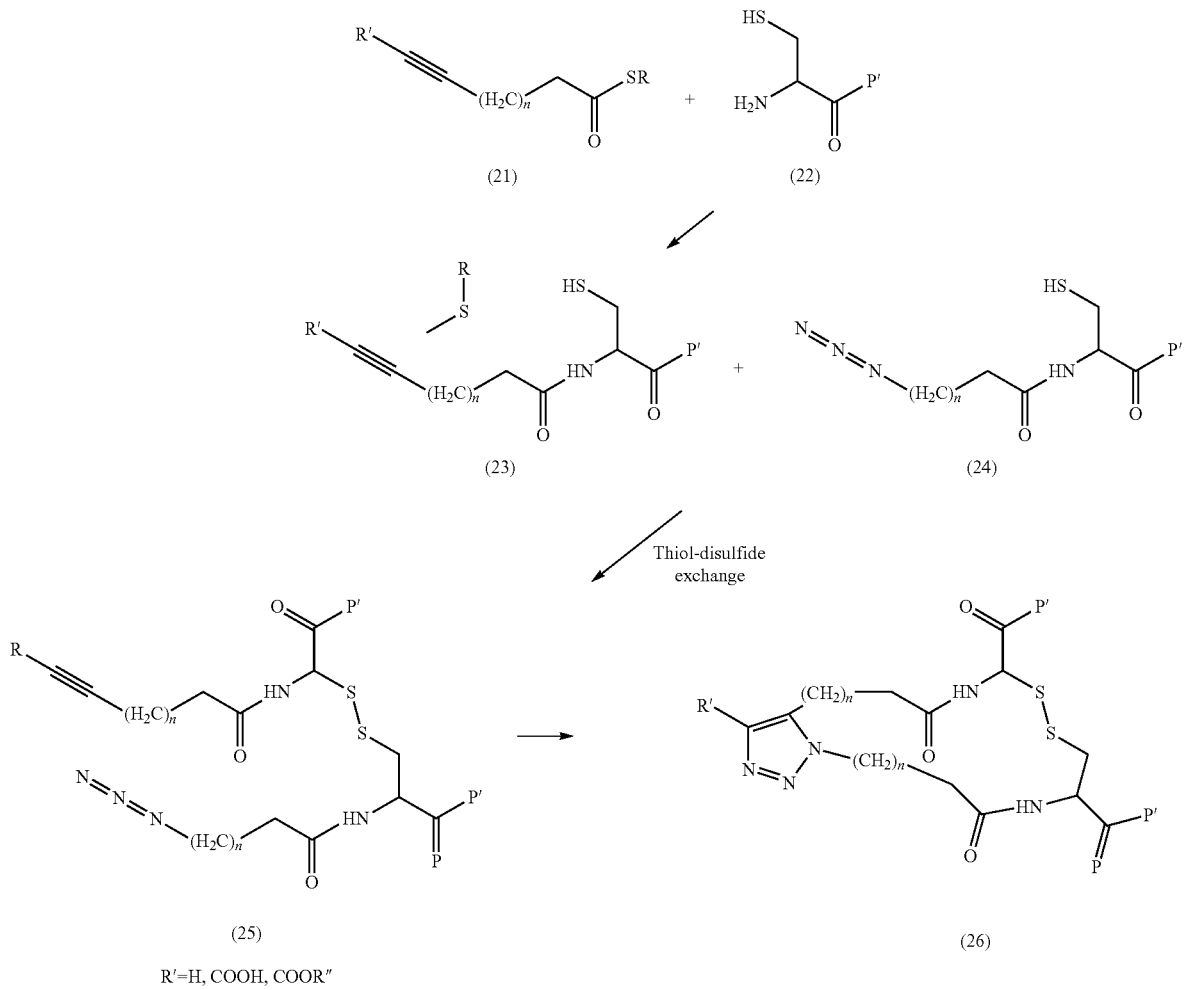

Scheme 6

R'=H, COOH, COOR″

Scheme 7

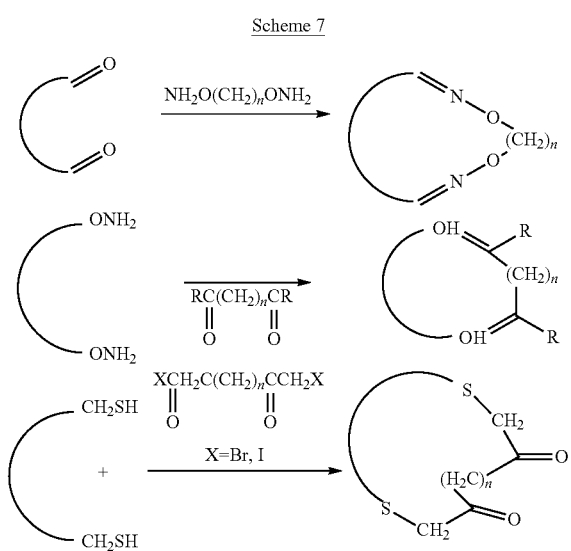

For example, residues 22-55 of leptin, VPIQKVQDDTKTLIKTIVTRINDISHTQSVSSKQK (SEQ ID NO: 1), can be used in these methods. The requisite functional groups can be installed using synthetic methods known in the art. For example, aldo- and keto-carbonyl groups can be installed using peptide synthesis methods known in the art or the transamination methods described herein and known in the art (see, e.g., Witus et al., *J. Am. Chem. Soc.*, 132:16812-7, 2010). Similarly, the aminooxy and thiol functionality can also be installed using peptide synthesis methods. When peptide synthesis methods are used, natural and unnatural amino acids can be used to provide the requisite functionality. Exemplary amino acids are shown in Scheme 8, where PG is H or an N-protecting group.

Scheme 8

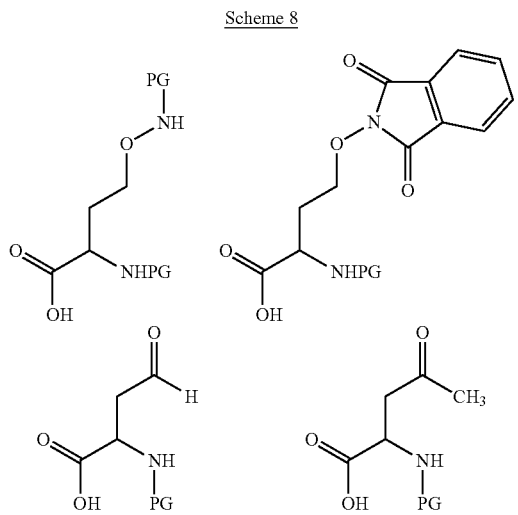

Facilitating Protein Dimer Formation Through "Dock and Lock" Mechanisms of α-Carbonyls During the course of implementing a route from α-carbonyl proteins (27) to covalently-linked protein dimers (32) (Scheme 9) mediated by the mono-oxime (28), it was found that certain α-carbonyl polypeptides such as leptin ketoamide (derived by transamination from leptin with an additional N-terminal alanine (A-leptin)), undergo very rapid dimerization to (29), a covalently linked species of a different type. Often, this type of dimer is difficult to obtain, and even reactions to form small molecule adducts of (27) (e.g., (28)), require many hours at high millimolar concentrations of (9) to go to completion. A rationale for this chemistry is found in precedents describing the pronounced tendency of many cytokine and chemokines (in signaling or chemotactic mechanisms) to aggregate, or associate as noncovalent dimers. Indeed, leptin is related to cytokine systems that are part of four helix bundle families (see, e.g., Ratsimandresy et al., *Curr Pharm Des.* 15:1998-2025, 2009, and Salanga et al., *Cell Mol Life Sci.* 66:1370-86, 2009, and references therein).

A rapidly established pre-equilibrium between monomeric and dimeric cytokines and structurally related systems provides a basis for bringing reactive components together rapidly and non-covalently. Provided that structural features that underlie non-covalent dimer formation are not compromised by chemical modification and that each protein component can achieve proper orientation for dimer formation, the bis-functionalized linker can irreversibly, covalently, and rapidly connect polypeptides or proteins by a combination of covalent and noncovalent forces. Utilizing leptin molecules with natural sequences, except for the addition of an N-terminal alanine, to facilitate α-carbonyl formation, we have prepared the ketoamide corresponding to transamination of leptin with N-terminal alanines.

Scheme 9

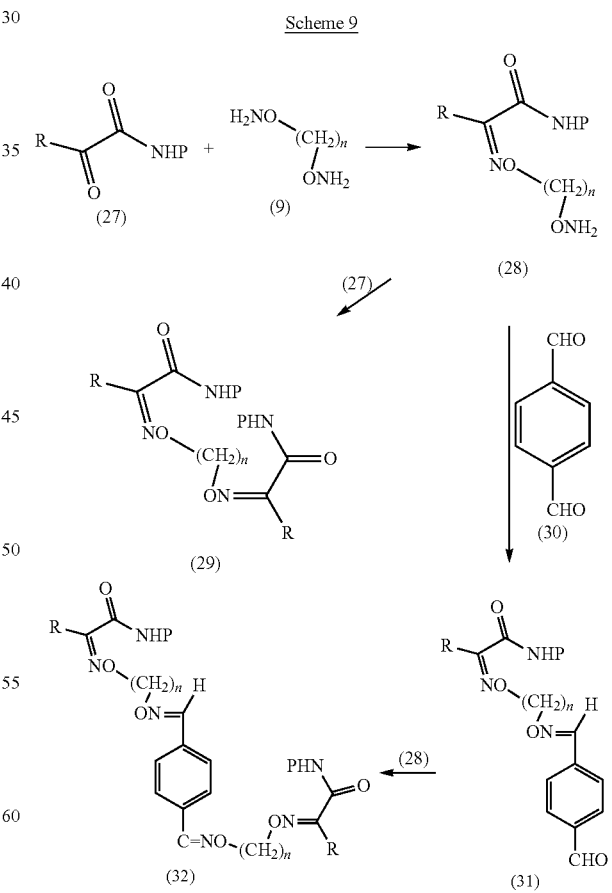

Quite remarkably, the leptin ketoamide corresponding to (27) has a stronger tendency to dimerize noncovalently than does the precursor leptin, although both dimers are detectable in gel filtration studies. When leptin ketoamide is treated with ω-bis-aminooxy molecules (9), the ketoamide compound dimerizes covalently and irreversibly. Among the many targets for dimer or multimer technology, members of the four helix bundle family, which are classified as short-chain and long chain groups (Rozwarski et al., *Structure*, 2:159-173, 1994), are of particular interest. Covalently-linked dimeric cytokines have the potential to be used as drugs as antagonists or agonists (see, e.g., Salanga et al., *Cell Mol Life Sci.* 66:1370-86, 2009).

In some instances, the cytokines and similar polypeptides can be modified at their N-terminus by transamination of an alanine or glycine residue that is either a normal part of the protein sequence or is appended to the normal N-terminus by recombinant methods (see, e.g., Rush et al., *J. Am. Chem. Soc.* 130:12240-1, 2008, and Witus, *J. Am. Chem. Soc.* 132:16812-7, 2010). Alternatively, the ligation technology described herein, can be used to incorporate α-oxacyl functions at the N-termini of protein frameworks or to install isolated ketone or aldehyde functional groups that are unconjugated to amide functions (see, e.g., compounds 4(d)-(f)). Established methods employing oxidative processes applied to serine side chains can also provide the requisite protein substrates for bis-oxime formation. Further, and in view of the leptin dimerization observed herein, new methods have been devised that can take advantage of cytokines having a tendency to dimerize non-covalently in order to form covalent links between such cytokines. These strategies can also be applied to the preparation of covalently linked dimers of other proteins and polypeptides.

The combination of biologically-based structural motifs that code for noncovalent dimers and site-specific chemistries orthogonal to peptide functionality provides a powerful generic basis for dimer and multimer synthetic design by "dock and lock" mechanisms. For example, the use of cytokine dimers as potential therapeutics can be extended in multimeric motifs that present pairs of cytokines on a molecular template. The construction of a tetramer of covalently-linked cytokines (38) is illustrated in Scheme 10 using the commercially available starting template 1,2,4,5-benzene-tetracarboxylic anhydride (33) in conjunction with aminooxy chemistries leading to tetra-oximinoethers ((38), structure not shown). Other substrates featuring the known tetrabromide ((39), m=1; Scheme 11) and routes involving sterically protected malonates (Scheme 12) can be employed as synthetic sequences directed towards the respective tetrameric cytokine systems (42), (49), and (52). Analogous routes utilizing hydrazine and hydrazide functions in place of aminooxy in these Schemes can also be used.

Scheme 10

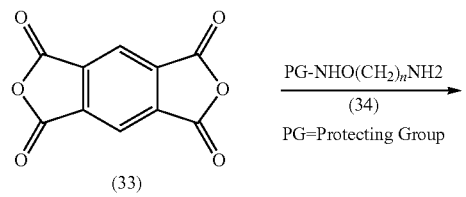
(33)

PG-NHO(CH$_2$)$_n$NH2
(34)
PG=Protecting Group

-continued

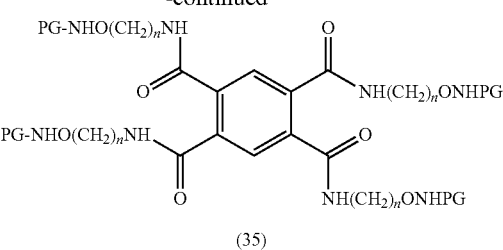
(35)

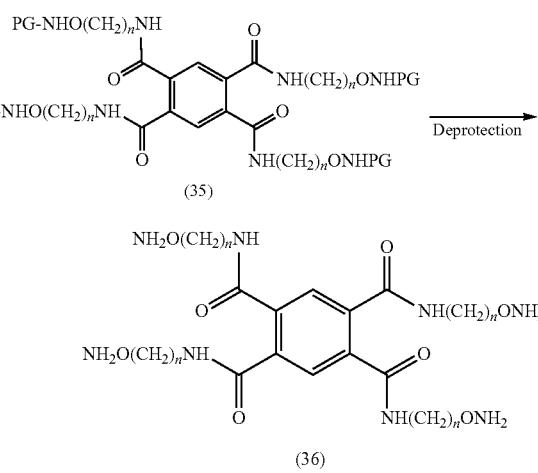
(35)

Deprotection

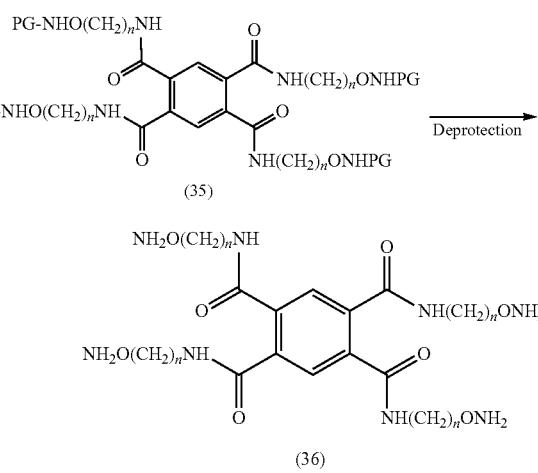
(36)

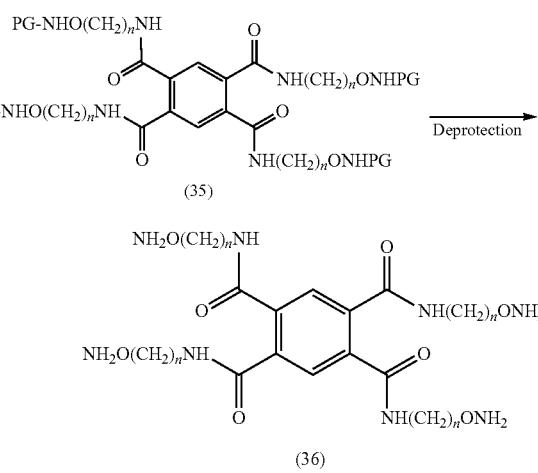
(36)

+

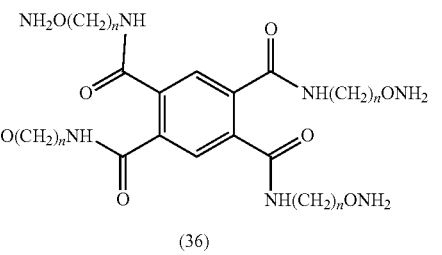
(37)
P=cytokine

⟶ Tetrameric cytokine (38)

Scheme 11

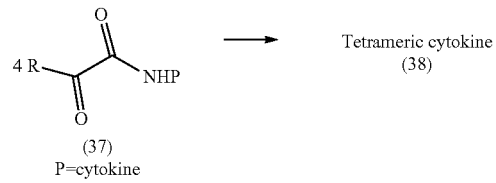
(39)

+ PG-NHO(CH$_2$)$_n$OK ⟶

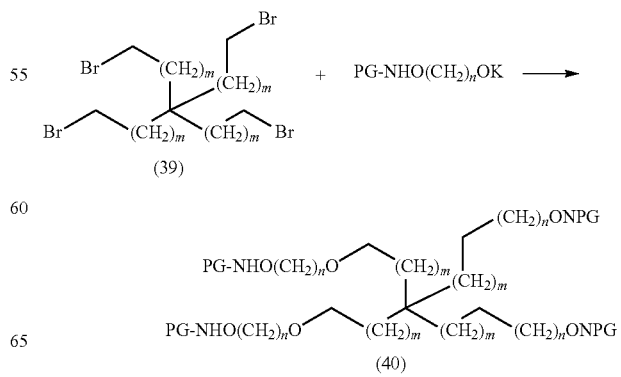
(40)

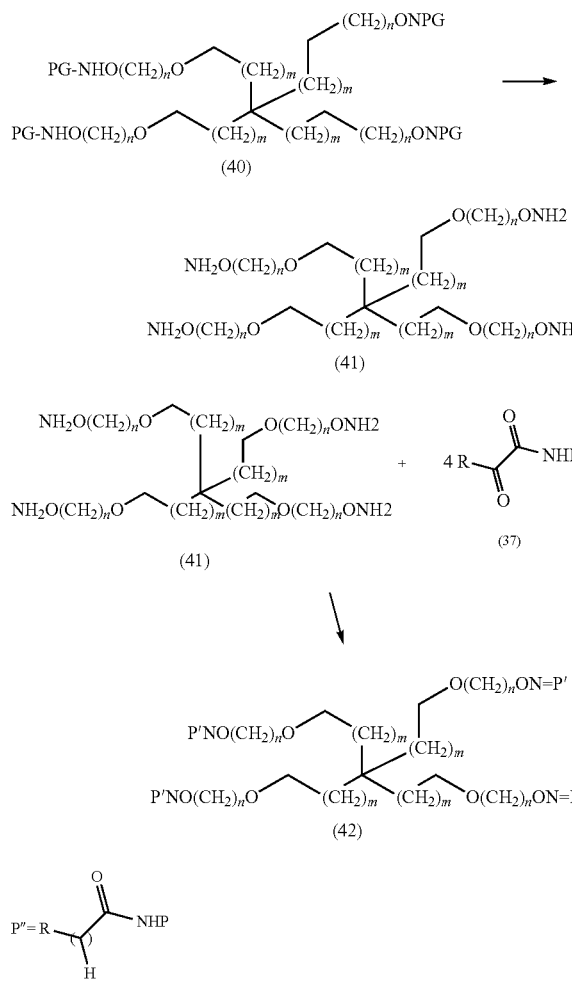

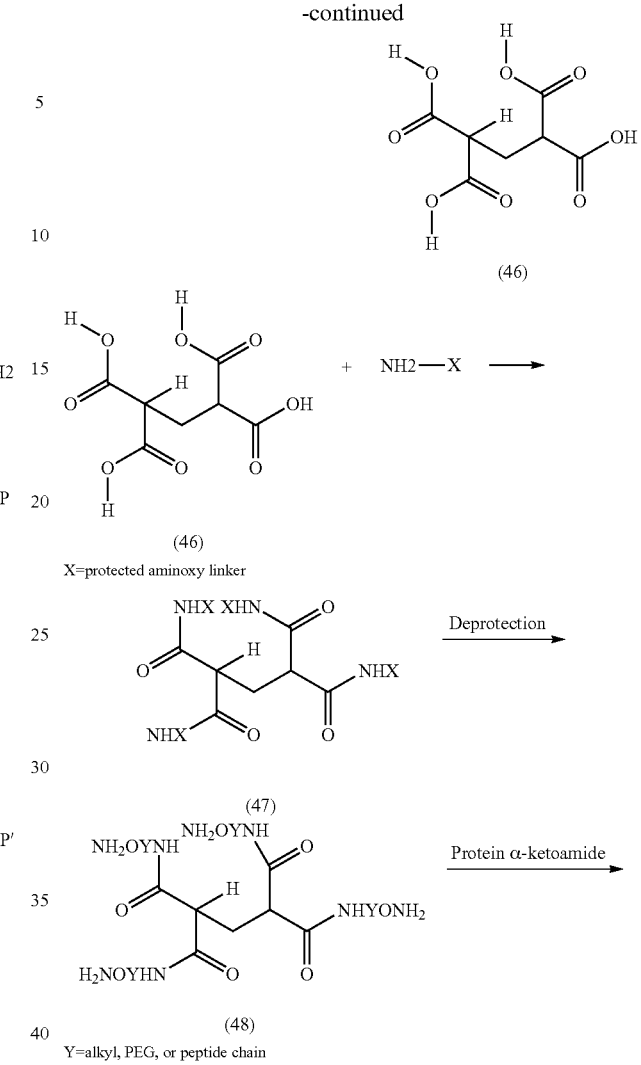

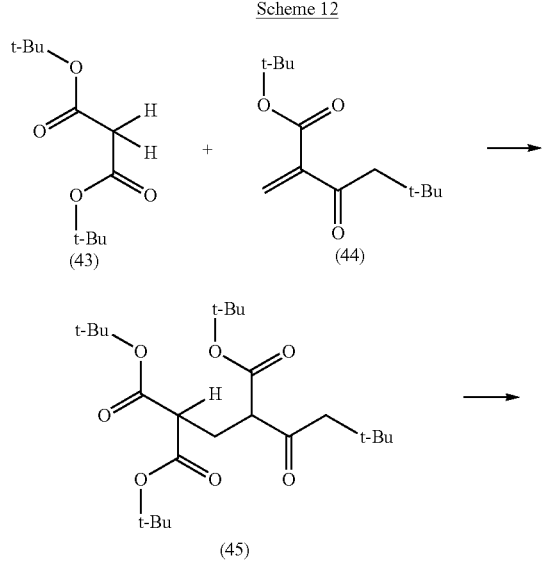

These approaches for exploiting proximity effects on organic templates through covalent linkers represent an alternative to fusion proteins (Schmidt et al., *Curr Opin Drug Discov Devel.* 12:284-95, 2009). The chemical modification methods described herein, however, can have broader applicability by employing a broad array of linkers and can occur at residues other than protein termini if the requisite elements are appropriately installed, The use of natural structural elements with established aggregation and associative properties can also be used to bring molecules together and position reaction partners in close approximation. This approach is not restricted to cytokine-based dimerization motifs. For example complementary sequences, including "zipper" motifs (e.g., leucine zippers as described in Vinson et al., *Mol Cell Biol.* 18:6321-35, 2002), and PNA zippers as described in Pensato et al., *Biopolymers*, 93(5):434-41, 2010) are known in the art as binding motifs that are capable of bring reaction pairs in close approximation. These motifs can be used to enable rapid or "spontaneous" coupling of acetylene/azide and thiol/maleimide, thiol/disulfide, and alkoxylamine/carbonyl pairs for "locking" separate entities or molecules together irreversibly.

Carbonyl-Targeted Technologies of Choice

The use of carbonyls as points of modification within protein targets has many potential benefits. As described herein, carbonyl functionality serve to extend protein frameworks in an efficient way via the ligation technology described herein. Additional strategies for attachment technologies that link commercially valuable biologically active agents (e.g., drug pharmacophores, spectroscopic probes or radiochemicals) to the protein target continue to be of interest.

For example, long reaction times for connecting biologically active agents to proteins at embedded carbonyl functionality are not uncommon, often on the order of many hours. Further, mixtures of syn- and anti-isomers are often formed giving rise to heterogeneous mixtures. Additionally, the doubly-bonded functions like oximes are difficult to reduce when they are incorporated within the protein framework. When carbonyls contiguous with peptide functions as generated via transamination of the N-terminal amino acid (see, e.g., Gilmore et al., vide supra), are treated with carbonyl reagents such as alkoxyl amines, large excesses of transaminating agent and overnight incubation times are required for high conversions.

By isolating carbonyls from normal peptide sequences with intervening alkyl or polyethylene glycol chains as non-peptidic linkers, we have been able to dramatically improve rates of carbonyl modification. Targeting carbonyls that are non-contiguous with the peptide chain as in Scheme 3 (e.g., (4(b), 4(c), 4(e), and 4(f)), apparently make them more accessible to chemical modification. Accordingly, we have applied our technology to create alternative sequences for attaching biologically active agents to α-carbonyl-amide linked proteins, each of which has a number of attributes and advantages. The various sequences are portrayed in Scheme 13 using bis-oxime reagents explicitly to represent other linker types, e.g. reactive elements: hydrazine, hydrazide; chains: peptide, PEG.

Scheme 13

Sequence A

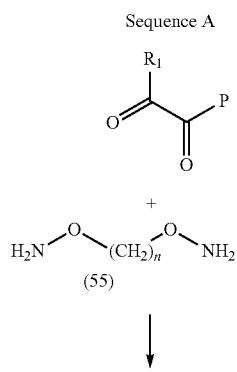

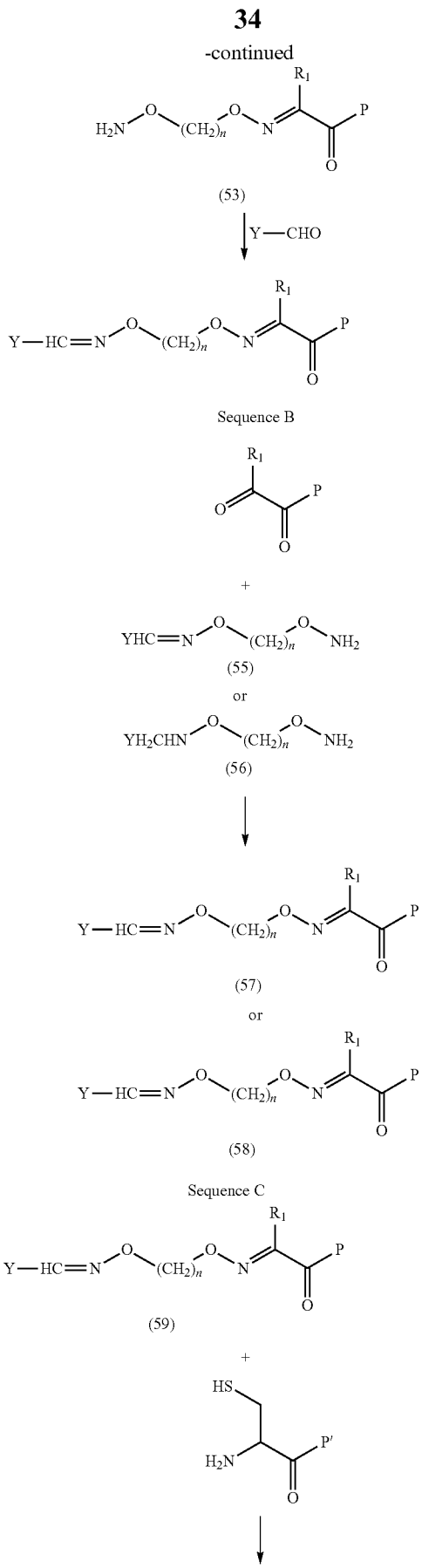

-continued

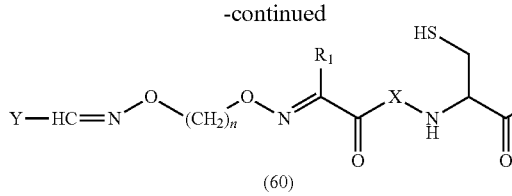

X= Linker

The modular sequence A requires the most manipulation of the protein and is the most limiting for modifications of the linker and the entity Y. For example, the protein-linked product is not easily modified once the final oxime linkage is established in (54). However, it is advantageous to have methods available by which biologically active agents can be linked to the protein in the final step of a synthetic sequence once an α-nucleophilic moiety has been established on the protein component. For example, sequence A is adaptable to the introduction of entities such as imaging agents containing radiolabels that must be rapidly linked to protein in a single step. Toward the end of facilitating a terminal step in a sequence involving a nucleophilic function in one component, we have developed ligation methods that rapidly introduce carbonyl functionality onto protein frameworks. Thus diketones, because of the greater stabilities of ketoximes over aldoximes, have been linking components of choice to aminooxy and the like. Further, bis-ketones such as penta-2,4-diones and hexa-2,5-diones have proved useful for forming relatively stable adducts with alkoxylamine functionality installed in proteins.

The utility of carbonyl chemistry in protein modification as directed towards protein conjugates is made manifest by pyruvate (R=CH$_3$, 61; Scheme 14), as a cross-linking agent. Pyruvate provides two functions that can be conveniently exploited economically. Pyruvate is particularly useful in that the carboxyl function can carry a variety of biologically active agents through amide formation (eq. 1), and, alternatively, the ketone carbonyl can provide a point of attack for attachment of biologically active agents to aminoxy, Scheme 14 (eq. 2). The carboxyl group in (61) can be activated in a variety of ways that are known in the art, to accept biologically active agents that are specifically linked to the carboxyl group. The resulting 2-oxacyl derivative can then be used to connect to amine, aminoxy and like nucleophiles that have been installed in the protein. A number of drugs such as doxorubicin and calicheamicin can be modified and linked to proteins via condensation with pyruvyl substrates as in Scheme 14, eq 1 (R=CH$_3$), followed by attachment to the protein at the α-carbonyl. Reaction with such carbonyls is facile and can be catalyzed by amines, particularly ethylenediamine, which we have discovered to be a preferable catalyst. Alternatively, the sequence of attachment can be inverted with the biologically active agent conjugated to the α-carbonyl and the carboxyl activated for attachment to the protein target as in eq. 2.

In special instances, where the protein contains accessible thiols, 3-bromopyruvate (66) or its carboxyl derivatives can be used to install a keto function in the protein as in Scheme 14, eq. 3.

Scheme 14

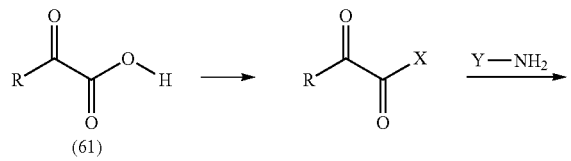

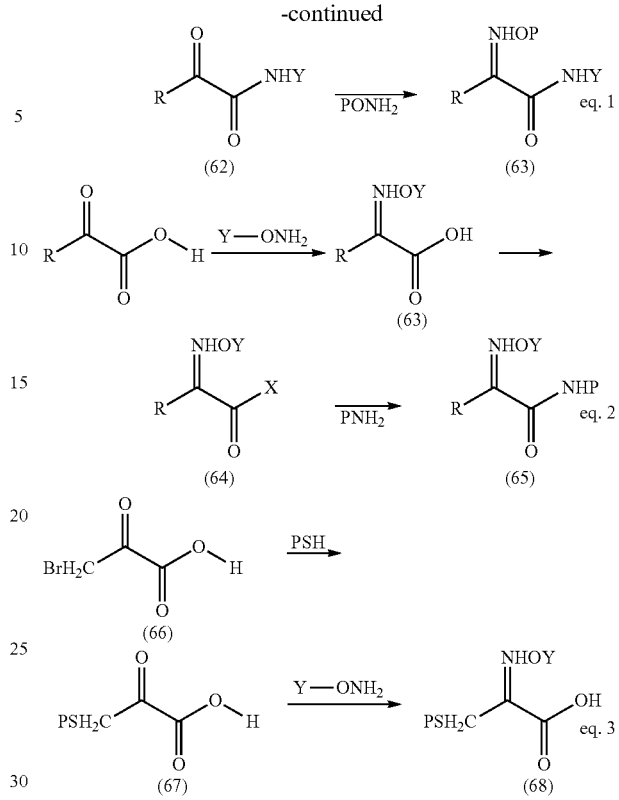

Peptides, Polypeptides and Proteins

Proteins, peptides, and polypeptides may be made by any technique known to those of skill in the art, including the expression of proteins, polypeptides or peptides through standard molecular biological techniques, the isolation of proteins or peptides from natural sources, or the chemical synthesis of proteins or peptides. Exemplary peptides, polypeptides, and proteins that can be used in the methods described herein are also described in, for example, U.S. Patent Publication No. 20100099649, which is herein incorporated by reference in its entirety.

Modified proteins can also be used in the methods described herein, where the native sequence or molecule is altered in such a way without materially altering the membrane binding affinity of the protein. Such modified proteins can be produced by chemical, genetic engineering, or recombinant techniques. The modification can include sequence modification through the addition of several amino acid residues, and/or an addition/deletion of an amino acid at a single site on the native or genetically engineered sequence. In the context of the present invention, modified proteins include proteins modified at the N-terminus by the addition of amino acid residues.

For example, a modified protein can have an amino acid sequence with at least one amino acid substitution (e.g., 2, 3, 4, 5, 6, 7, 8, 9, 10, 11, or 12 substitutions) compared to the naturally occurring sequence. The protein may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. Exemplary modifications include the introduction of a cysteine or alanine residue at the N-terminus. Alternatively, the modified protein has an amino acid sequence that has at least 35%, 40%, 50%, 60%, 65%, 70%, 75%, 80%, 85%, 90%, or 95% identity to the amino acid sequence of the naturally occurring peptide.

Four Helix Bundle Proteins

Four-helix bundle proteins typically include four helices packed in a coiled-coil arrangement, where the interfaces between the helices include mostly hydrophobic residues and the polar side chains on the exposed surfaces interact with the aqueous environment. Pairs of adjacent helices are often additionally stabilized by salt bridges between charged amino acids. Examples of four-helix bundle proteins include myohemerythrin, cytochromes (e.g., cytochrome c'), ferritin, tobacco mosaic virus coat protein, transcription factors, cytokines (e.g., human growth hormone), and Lac repressor C-terminal.

Cytokines

Helical cytokines are usually subclassified into short-chain, long-chain, and interferon groups based on their sequence length, the presence of additional short secondary structural elements within the loop regions, and the topology of the helix C to D loop. Exemplary helical cytokines include, but are not limited to: cardiotrophin-like cytokine NNT-1, ciliary neurotrophic factor, macrophage colony stimulating factor, granulocyte-macrophage colony stimulating factor, granulocyte colony-stimulating factor, cardiotrophin-1, erythropoeitin, FLT3 ligand, somatotropin, interon alpha-1, interferon beta, interferon gamma, interferon kappa, interferon tau-1, interferon omega-1, interleukin-2, interleukin-3, interleukin-4, interleukin-5, interleukin-6, interleukin-7, interleukin-9, interleukin-10, interleukin-11, interleukin-12 alpha chain, interleukin-13, interleukin-15, interleukin-19, interleukin-20, interleukin-21, interleukin-22, interleukin-23, interleukin-24, interleukin-26, interleukin-27, interleukin-28A (inteferon lambda-2), interleukin-29 (interferon lambda-1), interleukin-31, stem cell factor, leptin, leukaemia inhibitory factor, oncostatin M, prolactin, ciliary neurotrophic factor (CNTF), and thrombopoietin.

Leptin is an exemplary molecule possessing a cytokine helical fold. The leptin proteins used in the methods of the invention include naturally available leptin, commercially available leptin, analogs of leptin, in which one or more of the amino acid residues are replaced by different amino acid residues, or are deleted, or one or more amino acid residues are added to the original sequence of leptin without changing considerably the activity of the resulting products as compared with wild type leptin or its active fragments or fractions. The leptins used in the present invention can be prepared by known synthesis and/or by site-directed mutagenesis techniques, or any other known technique as appropriate.

Cytokines in Therapy

The role of cytokines in disease and other pathogenic conditions is the subject of extensive study. Therapeutic uses of cytokines are described in, e.g., Schreiber et al., *Curr. Opin. Chem Biol.* 14:511-9, 2010; Donnelly et al., *Annals of the New York Academy of Sciences*, vol. 1182, pages 1-13 (2009); Ratsimandresy et al., *Curr. Pharm. Des.* 15:1998-2025; and D'Acquisto et al., *Biochem. Pharmacol.,* 79:525-34, 2010). For example, inflammatory cytokines, particularly IL-12 family members, are thought to be involved in autoimmune disorders such as rheumatoid arthritis, lupus erythematosus, psoriasis, multiple sclerosis, type-1 diabetes, Crohn's disease, and systemic sclerosis(SS) (Kunz et al., *Mediators of Inflammation,* 1-20 (2009)). In addition to multiple sclerosis, the role of cytokines in other CNS disorders such as Alzheimer disease and fever has also been considered (Steinman, *J. Clin. Invest.* 118:3557-3563 (2008)). The role of cytokines in treatment of cancer has also been studied (see, e.g., Waller et al., *Cancer,* 97(7):1797-1809, 2003 (modulation of antitumor immune responses), and Kirkwood et al., *Clin. Cancer Res.* 12(7 Supp): 2331s-2336s; 2006 (treatment of melanoma)).

Cytokines are also thought to play a role in liver disease (e.g., Tilg, *Can. J. Gastroenterol.* 15:661-668, 2001), including alcoholic liver disease (e.g., Neuman, *Alcohol Res. Health,* 27(4):307-16, 2003). Further, cachexia (e.g., geriatric cachexia) is associated with increased concentrations of proinflammatory cytokines such as tumor necrosis factor alpha (TNF-alpha), interleukin (IL) 1, IL-6, serotonin, and interferon gamma (Yeh et al., *Am. J. Clin. Nutr.* 70:183-97, 1999). Accordingly, any of these conditions may be suitable targets for methods of treatment that include the multimeric proteins (e.g., dimeric cytokines) described herein.

The biological properties of cytokine dimers are also of interest (see, e.g., U.S. Pat. No. 6,685,932). It is thought that these compounds are likely chemoattractants and responsible for the recruitment of immune cells (i.e., immune cell trafficking). It is also possible that dimers can modulate cellular processes when covalently linked (e.g., Matthews et al., *Biochemistry,* 37(30):10671-80, 1998).

For these reasons, the multimeric (e.g., dimeric) cytokines described herein can be useful in methods of medical treatment. Exemplary molecules with cytokine helical folds that can be used in the methods described herein, as well as in methods of medical treatment, are shown in Table 1.

TABLE 1

| Cytokine | Indications Treatable With Agonists | Indications Treatable With Antagonists |
|---|---|---|
| IL-6 | — | Rheumatoid arthritis (RA) Inflammation |
| IL-11 | Thrombocyopenia | Crohn's disease Gastric Cancer |
| Human growth hormone (hGH) | Growth disorders GH deficiency | Type 1 diabetes |
| Leukemia inhibitory factor (LIF) | Multiple sclerosis (MS) | RA Cancer |
| G-CSF | Cerebral ischemia Neutropenia | — |
| Prolactin | — | Prolactinomas |
| Oncostatin M (OSM) | — | Obesity |
| Cardiotrophin-1 (CT-1) | Fulminant hepatic failure Amyotropic lateral sclerosis | Cardiac hypertrophy |

Biologically Active Agents

Biologically active agents that can be used in the methods described herein include therapeutic, diagnostic, and prophylactic agents. For example, immunoconjugates of the multimeric proteins (e.g., dimeric cytokines) can be prepared.

Therapeutic Agents

Exemplary classes of therapeutic agents include, but are not limited to carbohydrates, anti-microbials, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatroban, antibodies, neurotransmitters, psychoactive drugs, oligonucleotides, proteins, lipids, and combinations thereof.

Additional therapeutic agents that can be used in the methods described herein include, without limitation, growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutyric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an anti-inflammatory agent, such as an NSAID, corticosteriod, or COX-2 inhibitor, e.g., rofecoxib, celecoxib, valdecoxib, or lumiracoxib. The therapeutic agent may also include antibiotics.

Diagnostic Agents

Exemplary diagnostic agents which can be used in the methods described herein include, without limitation, imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials. Other diagnostic agents that can be used in the methods described herein include those described in U.S. Patent Publication No. 20100099649, which is herein incorporated by reference in its entirety.

Immunoconjugates

The invention also provides for the preparation of immunoconjugates and the use of these compounds, or compositions thereof, in methods of medical treatment. For example, any of the multimeric proteins described herein (e.g., dimeric cytokines) can further include an intact antibody fragment, a single-chain variable fragment (scFv), a diabody, a minibody, or a scFv-Fc fragment. The use of immunoconjugates allows for the targeted delivery of a therapeutic to particular cells (e.g., tumor cells; see, e.g., Mak et al., *Primer to the Immune Response*, page 277, Academic Press, 2008). Accordingly, the preparation and study of cytokine immunoconjugates is of great interest for developing new therapeutic methods. For example, a tumor-targeting antibody-(Interferon α) conjugate has been prepared and studied for efficacy in the treatment of lymphoma (Rossi et al., *Blood*, 114:3864-3871, 2009). Accordingly, such strategies may be applied to the present multimeric proteins (e.g., dimeric cytokines) for the targeted delivery of these compounds to a cell.

Scheme 15 shows an exemplary strategy that can be employed to prepare immunoconjugates of the multimeric proteins (e.g., dimeric cytokines) described herein.

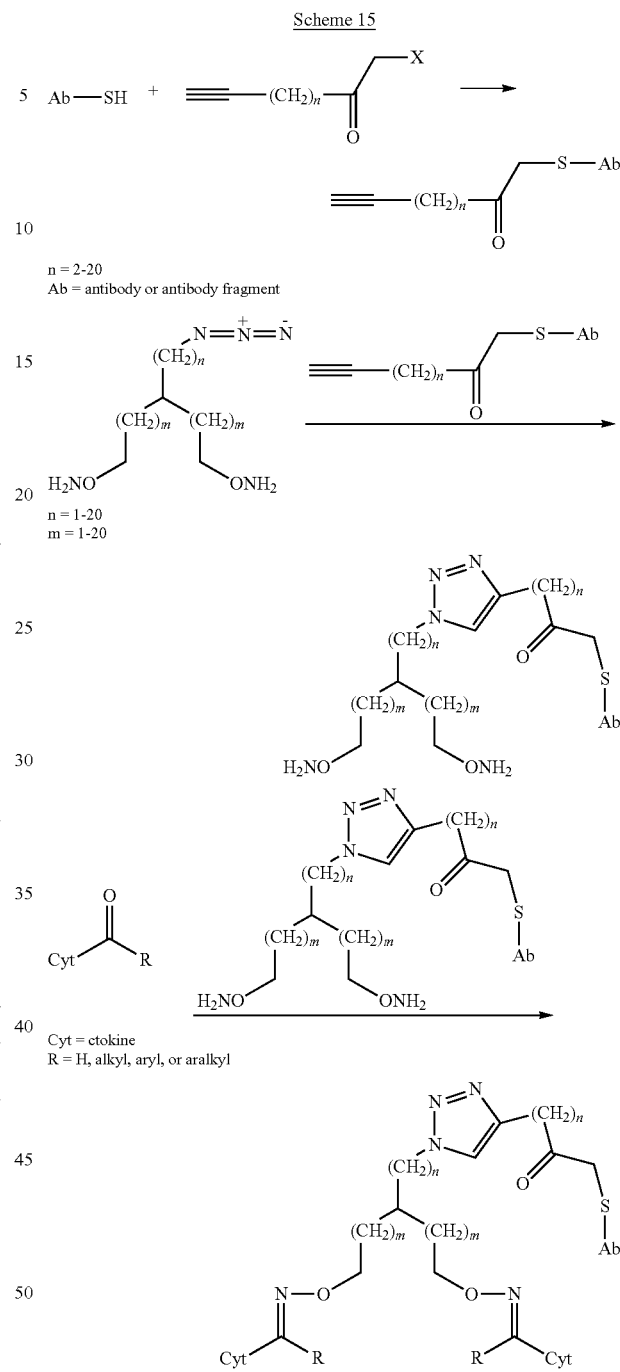

Scheme 15

In Scheme 15, an antibody or an antibody fragment that includes a thiol group can be alkylated with a fragment that includes an alkynyl group. Next, the alkynyl group can undergo a Huisgen cycloaddition reaction with a bifunctional linker (e.g., a bis-aminooxy group) that also includes an azido group. The resultant product can then be treated with a protein (e.g., a cytokine) having a carbonyl functional group in order to produce the immunoconjugate shown in this scheme. In variants of this scheme, after the first condensation, the ketone can be reduced and carried through as an alcohol. Protection-deprotection strategies involving the aminoxy groups can also be employed in these methods.

EXAMPLES

Transamination of A-Leptin by Pyridoxal Phosphate (PLP) and Cross-Linking Experiments

For protein modification studies of the four α-helical-bundle protein A-leptin (A), pyridoxal phosphate (PLP, B) as a transaminating agent with the objective of producing a carbonyl at the N-terminus (Scheme 16). When A-leptin is incubated with 10 mM PLP in PBS, pH 6.5 at 37° C. for 16 hr, three peaks are observed in the mass spectrum at 16,095, 16,342, and 32,189 Da. These signals can be related to a pyruvyl protein, the ketoamide (C). The product (D) with mass 16,342 corresponds to the sum of the masses of PLP (B) and the expected ketoamide (C).

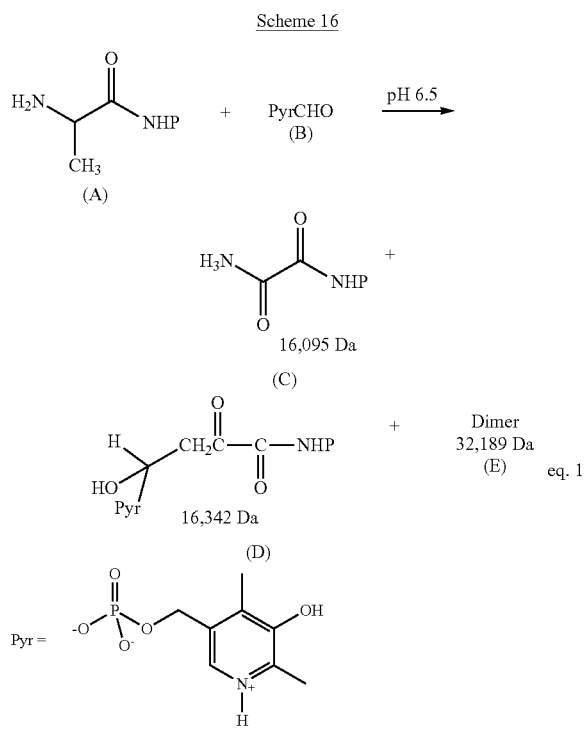

Dedeo et al. (11) have suggested an aldol structure for such adducts that are formed between PLP and pyruvyl proteins during transamination sequences. The high concentration of PLP and the potentially reactive pyruvyl protein (3), make the aldol product (4) a likely possibility in the case of A-leptin as well.

The peak at mass 32,189 formally corresponds to a dimer (C) of the pyruvyl protein (3). The dimer, as well as the presumed A-leptin-PLP adduct, is sensitive to basic conditions: within 2 hours at pH 9.0, the adduct completely converts to a cleavage product.

Indeed, when the pyruvyl protein (C) is treated with bis-α,ω-aminoxyalkanes (50-100 mM bis-α,ω-aminoxy (NH$_2$O(CH$_2$)$_n$ONH$_2$, n=5-7 (F)), pH 6.5, PBS, room temperature, 16 hr), in addition to mono-oxime adducts (G), covalent dimers (H) are formed (Scheme 17) as deduced from mass spectrometric data.

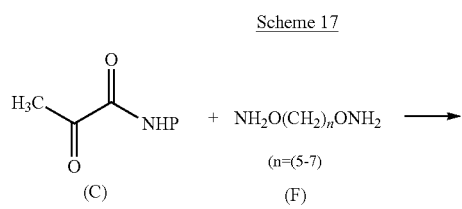

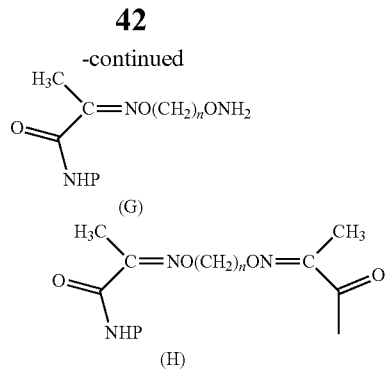

Quite remarkably, under very high millimolar concentrations (100 mM) of (16), cross-linking of the ketoamide (C, 10 μM) to form dimer H where n is 6 (J), competes effectively with ketoamide conversion to the mono-oxime.

Since A-leptin represents a molecular system in flux between monomers and dimers, experiments were undertaken to crosslink leptin monomers without prior modification of the alanine N-terminus using a bis-amine reactive regent. While dimerization of methionyl-leptin monomers (M-leptin) has been shown (see, e.g., U.S. Pat. Nos. 5,900,404; 6,204,247; and 6,420,340) using substoichiometric amounts of the bis-acylating agent, ethylenediamine-tetraacetic dianhydride, the products of cross-linking of M-leptin have masses which deviate from the theoretical as reported. Our experiments confirm that the masses of cross-linked M-leptin products fall in the dimer range and, further, show that analogous reactions of A-leptin have similar mass spectrometry profiles.

When A-leptin was treated with 0.75 fold molar equivalent of EDTA$^2$, in pH 7.0, PBS at 4° C. after 2 hours, the parent protein is ~40-50% converted to multiple peaks in both the monomer and dimer ranges. In the dimer range, two peaks are observed at 32,501 (major peak) and 32,809 (minor peak), respectively. The expected mass of the leptin dimer linked by an EDTA$^2$ molecule would be 16,095×2+256=32,446. After standing for 4 hours and then overnight, greater conversion of the parent occurs, but the spectral pattern is similar to what has been observed after 2 hours. Accordingly, the chemical activity of A-leptin under dimerization conditions and without need to install an α-carbonyl reactive group can be applied to the functionalization of other proteins that can self-dimerize or self-aggregate (e.g., to form covalently linked dimers).

Comparison of Leptin Dimerization to Dimerization of Myoglobin

The observed chemical reactivity of leptin can also be contrasted with the requirements to form myoglobin dimers. The transamination of horse heart myoglobin with pyridoxal phosphate yields the N-terminal aldehyde that is present as the hydrate. The oxidation product was then treated with bis-1,6-aminoxyhexane: in sharp contrast to the leptin system, no trace of dimer was observed over a span of 16-24 hours. Treatment of the monooxime that does form under these conditions with terephthaldehyde results in the extension of the N-terminus and incorporate a free aldehyde group on the protein surface. Such extended networks with terminal aldehyde functions are known to react quantitatively within minutes when treated with low millimolar concentrations of small molecule aminoxy substrates. Accordingly, these conditions therefore allow the formation of myoglobin dimers. Further, reaction of myoglobin with EDTA$^2$ under the substoichiometeric conditions described herein for dimerization of A-leptin produces only singly labeled products.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of site specifically producing a covalently linked multimeric protein comprising:
   (i) providing one or more proteins, wherein said one or more proteins is:
      (a) a four helix bundle protein or comprises a zipper binding motif;
      (b) in the form of a multimer, wherein said one or more proteins are non-covalently bound to each other within said multimer; and
      (c) a polypeptide comprising a glycine or alanine residue at the N-terminus; and
   (ii) combining a bifunctional linker and said one or more proteins, wherein said bifunctional linker forms a covalent bond to said glycine or alanine residue in each protein to produce a covalently linked multimer, and wherein said bifunctional linker comprises two or more carbonyl groups.

2. The method of claim 1, wherein said multimer is a dimer.

3. The method of claim 1, wherein said bifunctional linker is a bis-anhydride or bis-carbonyl imidazole.

4. A method of site specifically producing a covalently linked multimeric protein comprising:
   (i) providing one or more proteins in the form of a multimer, wherein said one or more proteins are non-covalently bound to each other within said multimer, each one of one or more proteins comprising an α-carbonyl amide moiety; and
   (ii) combining a bifunctional linker and said one or more proteins, wherein said bifunctional linker (a) forms a covalent bond to the α-carbonyl amide moiety in each one of said one or more proteins and (b) comprises two or more carbonyl reactive functional groups.

5. The method of claim 4, wherein said carbonyl reactive functional group is selected from the group consisting of aminoxy, hydrazine, and semicarbazide groups.

6. The method of claim 4, wherein the nitrogen atom of said α-carbonyl amide moiety is the nitrogen atom of the N-terminal amino acid in each of said one or more proteins.

7. The method of claim 4, wherein said one or more proteins is annexin, granulocyte macrophage colony-stimulating factor, human superoxide dismutase, leptin, myoglobin, albumin, or avidin.

8. The method of claim 7, wherein said one or more proteins is annexin.

9. The method of claim 4, wherein
   (i) said bifunctional linker is a bis-aminooxyalkane $NH_2O(CH_2)_nONH_2$ where n is an integer between 1-20;
   (ii) said bifunctional linker is a bis-hydrazino-alkane $NH_2NH(CH_2)_nONHNH_2$ where n is an integer between 1-20; or
   (iii) said bifunctional linker is a bis-semicarbazide-alkane $NH_2NRCO(CH_2)_nOCNRNH_2$ where n is an integer between 1-20; or
   (iv) said bifunctional linker comprises a 1,ω-substituted polyethylene glycol polymer comprising up to 1000 monomeric moieties.

* * * * *